United States Patent
Gonzalez

(10) Patent No.: US 11,291,361 B2
(45) Date of Patent: Apr. 5, 2022

(54) IMAGE PROCESSING METHOD AND SYSTEM FOR EDGE DETECTION AND LASER EYE SURGERY SYSTEM INCORPORATING THE SAME

(71) Applicant: AMO Development, LLC, Santa Ana, CA (US)

(72) Inventor: Javier Gonzalez, Palo Alto, CA (US)

(73) Assignee: AMO Development, Inc., Santa Ana, CA (US)

(*) Notice: Subject to any disclaimer, the term of this patent is extended or adjusted under 35 U.S.C. 154(b) by 234 days.

(21) Appl. No.: 16/724,019

(22) Filed: Dec. 20, 2019

(65) Prior Publication Data
US 2020/0121178 A1    Apr. 23, 2020

Related U.S. Application Data

(62) Division of application No. 14/969,452, filed on Dec. 15, 2015, now Pat. No. 10,548,470.
(Continued)

(51) Int. Cl.
*A61B 3/00*    (2006.01)
*A61B 3/10*    (2006.01)
(Continued)

(52) U.S. Cl.
CPC .......... *A61B 3/0025* (2013.01); *A61B 3/0033* (2013.01); *A61B 3/102* (2013.01);
(Continued)

(58) Field of Classification Search
CPC ....... A61B 3/0025; A61B 3/0033; A61B 3/14; A61B 3/0041; A61B 3/1005; A61B 3/102; A61B 3/1025; A61F 9/0084; A61F 2009/00846; A61F 2009/00851; A61F 2009/00889; G06T 7/162; G06T 7/11; G06T 2207/10101; G06T 2207/30041
(Continued)

(56) References Cited

U.S. PATENT DOCUMENTS 5,459,570 A    10/1995 Swanson et al.
5,720,894 A    2/1998 Neev et al.
(Continued)

OTHER PUBLICATIONS

Dijkstra E.W., "A Note on Two Problems in Connexion with Graphs," Numerische Mathematlk, 1959, vol. 1, pp. 269-271.
(Continued)

*Primary Examiner* — Aaron F Roane
(74) *Attorney, Agent, or Firm* — Johnson & Johnson Surgical Vision, Inc.

(57) ABSTRACT

A method of imaging an object includes obtaining an image data set from a raster scan. The image data set has a plurality of data points, each data point having an associated location and intensity; generating a reduced data set by selectively removing one or more data points from the image data set based upon an assigned probability of retaining the one or more data points in the data set, the assigned probability being a function of the intensity of a data point; generating a triangulation graph as a planar subdivision having faces that are triangles, the vertices of which are the data points and the edges of which are adjacent vertices; and segmenting the triangulated data set by finding a path with lowest cost between that vertex and every other vertex, wherein the cost is a function of the respective intensity of the vertices.

20 Claims, 12 Drawing Sheets

Related U.S. Application Data

(60) Provisional application No. 62/190,217, filed on Jul. 8, 2015.

(51) Int. Cl.
*G06T 7/11* (2017.01)
*G06T 7/162* (2017.01)
*A61B 3/14* (2006.01)
*A61F 9/008* (2006.01)

(52) U.S. Cl.
CPC .......... *A61B 3/1005* (2013.01); *A61B 3/1025* (2013.01); *A61B 3/14* (2013.01); *A61F 9/0084* (2013.01); *G06T 7/11* (2017.01); *G06T 7/162* (2017.01); *A61B 3/0041* (2013.01); *A61F 2009/00846* (2013.01); *A61F 2009/00851* (2013.01); *A61F 2009/00889* (2013.01); *G06T 2207/10101* (2013.01); *G06T 2207/30041* (2013.01)

(58) Field of Classification Search
USPC ............................................................ 606/4
See application file for complete search history.

(56) References Cited

U.S. PATENT DOCUMENTS

| | | |
|---|---|---|
| 5,748,352 A | 5/1998 | Hattori |
| 5,748,898 A | 5/1998 | Ueda |
| 5,957,915 A | 9/1999 | Trost |
| 5,984,916 A | 11/1999 | Lai |
| 6,019,472 A | 2/2000 | Koester et al. |
| 6,053,613 A | 4/2000 | Wei et al. |
| 6,111,645 A | 8/2000 | Tearney et al. |
| 6,454,761 B1 | 9/2002 | Freedman |
| 7,655,002 B2 | 2/2010 | Myers et al. |
| 7,683,914 B1 | 3/2010 | Cote |
| 7,717,907 B2 | 5/2010 | Ruiz et al. |
| 8,262,646 B2 | 9/2012 | Frey et al. |
| 8,350,183 B2 | 1/2013 | Vogel et al. |
| 8,382,745 B2 | 2/2013 | Naranjo-Tackman et al. |
| 8,414,564 B2 | 4/2013 | Goldshleger et al. |
| 2006/0008144 A1 | 1/2006 | Prasad et al. |
| 2011/0319873 A1 | 12/2011 | Raksi et al. |
| 2011/0319875 A1 | 12/2011 | Loesel et al. |

OTHER PUBLICATIONS

Thomas H.C., et al., "Section 24.3: Dijkstra's Algorithm," in: Introduction to Algorithms, 2001, Second Edition, MIT Press and McGraw Hill, pp. 595-601.

IMAGE PROCESSING METHOD AND SYSTEM FOR EDGE DETECTION AND LASER EYE SURGERY SYSTEM INCORPORATING THE SAME

RELATED APPLICATIONS

This application is a divisional of and claims priority to U.S. patent application Ser. No. 14/969,452, filed Dec. 15, 2015, which is a non-provisional application and claims the benefit under 35 U.S.C. § 119(e) of U.S. Provisional Application Ser. No. 62/190,217, filed Jul. 8, 2015, which is incorporated herein in its entirety by reference.

BACKGROUND

A number of techniques have been developed to detect an edge, boundary or layer in image data. The process for locating these features in an image is sometimes referred to as segmentation or edge detection. Conventional image processing systems and methods for edge detection in ophthalmic applications are generally predicated on obtaining and processing a rectangular data set, i.e., a data set 600 comprising an orderly array of image data points having i rows and j columns as shown in FIG. 1. The data set may be composed of, for instance, pixels. However, in some ophthalmic imaging applications, such as "across the cut" incisions, the scanning is done along a conical surface, such as the conical surface 602 shown in FIG. 1. Applying a rectangular data set to a conical surface leads to complications and difficulties in implementing a raster scan and displaying the processed image.

Specifically, as shown in FIG. 1, a rectangular data set 600, when applied to a conic surface results in an irregular spacing of the data points in successive rows along the radial coordinate, r, in conical space. As such, data points at large radial values are spaced at greater distances than are data points at lower values of r. In pulsed laser imaging systems, this means that the scan speed and/or pulse repetition rate must be finely controlled on a line by line basis in order to ensure that the collected image data is rectangular. This results in complex and difficult raster scan over the area to be imaged. Further, an excessive number of data points may be collected at some portions of the area to be imaged for the required resolution of the image due to the requirement that the collected data be in a rectangular format. This can lead needlessly large and lengthy calculations. Further, the resulting image obtained from a rectangular image data set applied to a conical surface may also be distorted because the displayed image 604 is displayed on a graphical user interface is usually provided as a rectangular image in which spacing between data sets in all the rows is substantially the same.

Improved image processing systems and methods are therefore needed that provide improved detection of edges, boundaries and layers in the imaged object while decreasing computation size and time, provide for simpler and faster raster scanning along conical surfaces and increase the precision of the displayed image.

SUMMARY

Hence, to obviate one or more problems due to limitations and disadvantages of the related art, this disclosure provides many embodiments relating to imaging and image processing, and more specifically, to systems and methods for segmentation and identification of edges, boundaries or layered objects in images.

In many embodiments, the presently disclosed subject matter discloses systems and methods for segmenting and identifying edges, boundaries or layered structures in ocular images. The imaged structures may be segmented using selective data reduction techniques, triangulation and segmentation in a manner that significantly reduces the processing time required for image segmentation, feature extraction or identification and the design of raster scans. It should be understood that although the disclosed systems and methods are applied to ocular images, the systems and methods may be applied to any images of an object having features to be segmented or identified.

A method of imaging an object, preferably a human eye, according to may embodiments comprises obtaining an image data set from a raster scan of the object, the image data set comprising a plurality of data points, each data point having a location and intensity associated with it; generating a reduced data set by selectively removing one or more data points from the image data set based upon an assigned probability of retaining the one or more data points in the data set, the assigned probability being a function of the intensity of a data point; generating a triangulation graph of the reduced data as a planar subdivision, preferably a maximal planar subdivision, having faces that are triangles, the vertices of which are the data points of the reduced data set and the edges of which are adjacent vertices; and segmenting the triangulation graph by finding a path with lowest cost between vertices of the triangulation graph, wherein the cost between vertices is a function of the respective intensity of the vertices. The raster scan is preferably conducted by scanning a pulsed laser along the object to be imaged and detecting back-reflected light from the object.

In many embodiments, the method includes reducing the image data set by a reduction factor prior to the selective removing step. In many embodiments, the method further comprises truncating at least one of the image data set and the reduced data set by removing data outside nominal biologic limits from the selected data set.

The triangulation graph is preferably a Delaunay graph of the reduced data set.

Preferably, the lowest cost path is found using a Dijkstra algorithm. The cost associated with between a first vertex having an intensity $I_1$ and a second vertex having an intensity $I_2$ is preferably given by the formula $$\text{Cost} = \frac{1}{(I_1 + I_2)/2}.$$

The method preferably including displaying the segmented data set on a graphical user interface.

A system for imaging an object in many embodiments comprises a memory for storing a plurality of instructions and a processor for executing the instructions to perform a plurality of steps. The instructions comprise the instructions for: obtaining an image data set from a raster scan of the object, the image data set comprising a plurality of data points, each data point having a location and intensity associated with it; generating a reduced data set by selectively removing one or more data points from the image data set based upon an assigned probability of retaining the one or more data points in the data set, the assigned probability being a function of the intensity of a data point; generating a triangulation graph of the reduced data as a planar subdivision, preferably a maximal planar subdivision, having faces that are triangles, the vertices of which are the data points of the reduced data set and the edges of which are adjacent vertices; and segmenting the triangulation graph by finding a path with lowest cost between that vertex and every other vertex, wherein the cost is a function of the respective Intensity of the vertices.

In many embodiments, the instructions include instruction for reducing the image data set by a reduction factor prior to the selective removing step. In many embodiments, the instructions further comprise instructions for truncating at least one of the image data set and the reduced data set by removing data outside nominal biologic limits from the selected data set.

The triangulation graph is preferably a Delaunay graph of the reduced data set.

Preferably, the instructions include instructions finding the lowest cost path using a Dijkstra algorithm. The cost associated with between a first vertex having an intensity $I_1$ and a second vertex having an intensity $I_2$ is preferably given by the formula $$\text{Cost} = \frac{1}{(I_1 + I_2)/2}.$$

Preferably, the instructions include instructions for displaying the segmented data set on a graphical user interface.

In many embodiments, a laser surgical system, preferably a laser eye surgical system, comprises the image processing system described herein.

A laser surgical system for imaging an object, preferably a human eye, comprises a laser source for generating a pulsed laser beam; an imaging system comprising a detector; shared optics configured for directing the pulsed laser beam to an object to be sampled and confocally deflecting back-reflected light from the object to the detector; and a controller operatively coupled to the laser source, the imaging system and the shared optics. The controller is configured to:
  (a) scan the pulsed laser beam in a raster scan along the object to be imaged;
  (b) collect an image data set corresponding to the intensity of the back-reflected light from each of the laser pulses, the image data set comprising a plurality of data points, each data point having a location and intensity associated with it;
  (c) generate a reduced data set by selectively removing one or more data points from the image data set based upon an assigned probability of retaining the one or more data points in the data set, the assigned probability being a function of the intensity of a data point;
  (d) generate a triangulation graph of the reduced data as a planar subdivision, preferably a maximal planar subdivision, having faces that are triangles, the vertices of which are the data points of the reduced data set and the edges of are adjacent vertices; and
  (e) segment the triangulation graph by finding a path with lowest cost between that vertex and every other vertex, wherein the cost is a function of the respective Intensity of the vertices.

The controller is preferably configured to reduce the image data set by a reduction factor prior selective removal of the one or more data points. The controller is also preferably configured to truncate at least one of the image data set and the reduced data set by removing data outside nominal biologic limits from the selected data set.

The triangulation graph is preferably a Delaunay graph of the reduced data set.

The lowest cost path is preferably found using a Dijkstra algorithm. Preferably, a cost associated with a first vertex having an intensity $I_1$ and a second vertex having an intensity $I_2$ is given by the formula $$\text{Cost} = \frac{1}{(I_1 + I_2)/2}.$$

The controller is preferably configured to display the segmented data on a graphical user interface.

One advantage of the present invention is that the image data set obtained by the raster scan is not required to be rectangular, in fact, the imaging processing method and system can process a data set of any shape, including a random shape. This permits greater flexibility, simplicity and speed in the design of the raster scan or the tissue to be imaged because the resulting data set need not be rectangular. The raster scan on a contoured surface may be done at, for instance, equal distances, thus simplifying the raster scan of the contoured surface. Further, scan speeds can be increased because the required precision of the raster scanner apparatus is reduced because the system is not constrained by the need to collect image data in the form of a structured data array.

Another advantage of the image processing methods and systems of many embodiments is that they provide faster and more precise imaging by selectively removing data points from the image data set that are unlikely to contain image information while simultaneously retaining data points in the data set that are likely to contain image information.

The resulting image produced by the image processing methods and systems is also more precise. For instance, when images are taken along the surface of cone, the resulting image is distorted when plotted in a rectangular format. However, the images of the present format are not rectangular and are free of the distortion caused by representing conic cross-section as rectangles.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

BRIEF DESCRIPTION OF THE FIGURES

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

DETAILED DESCRIPTION

Figure 1:
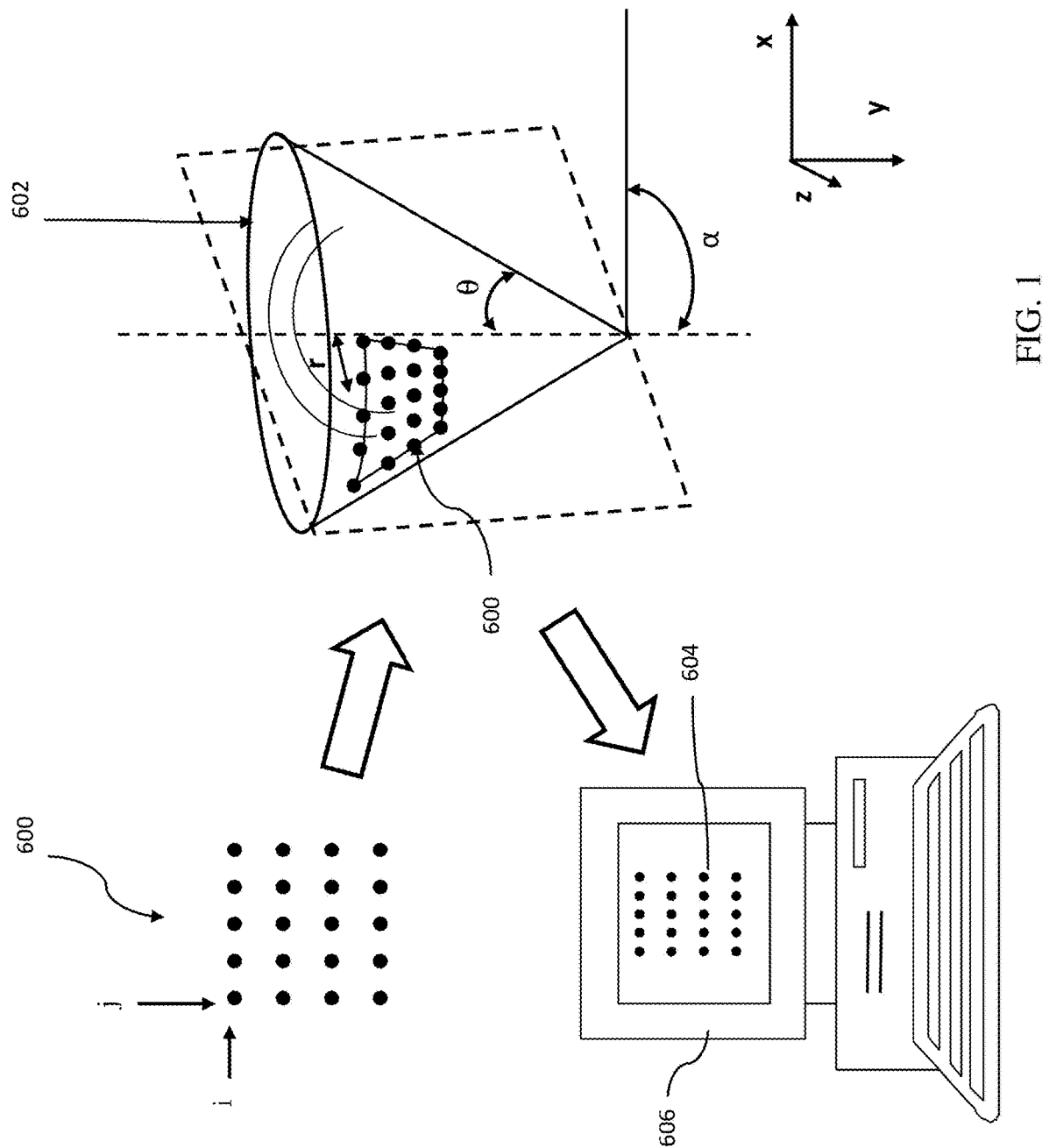
FIG. 1 is a graphical representation of aspect of using rectangular data sets in scanning conical sections.
Figure 2:
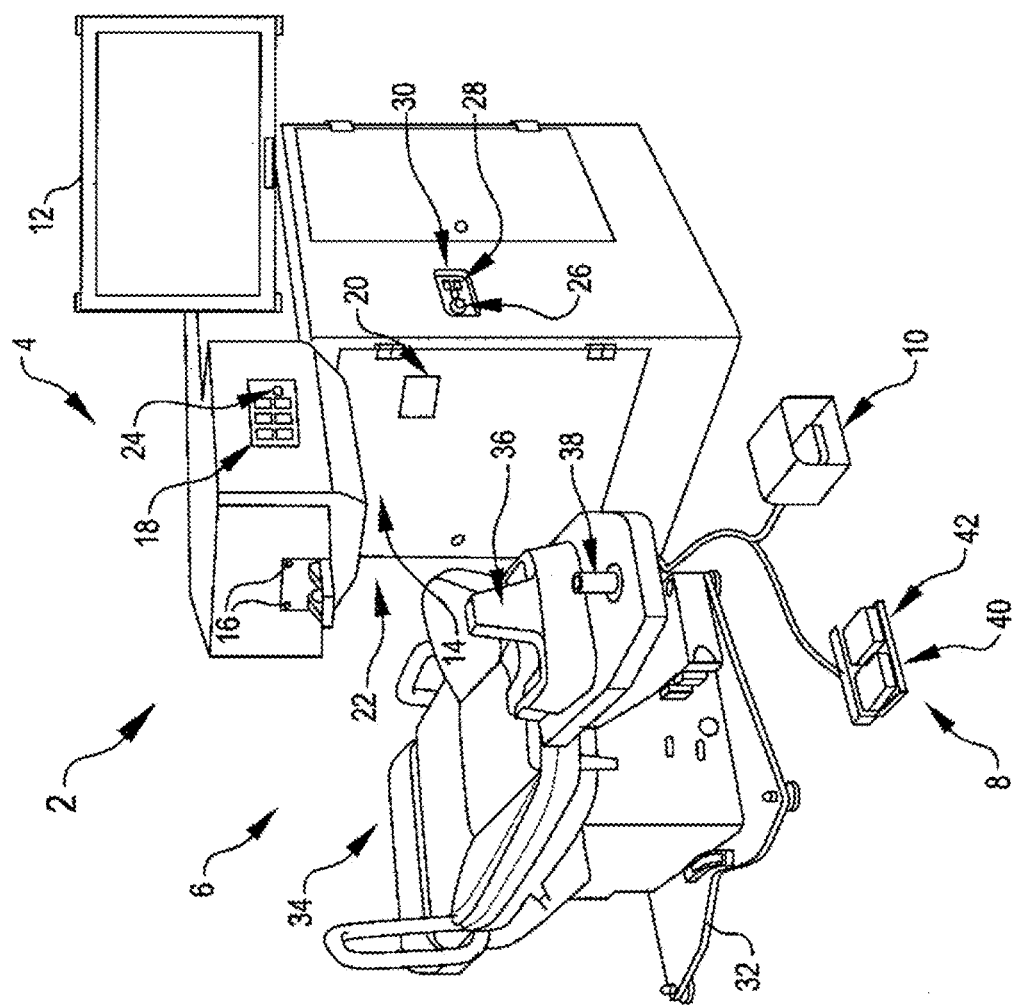
FIG. 2 shows a laser eye surgery system according to many embodiments.

FIG. 2 shows a laser eye surgery system 2, in accordance with many embodiments, operable to form precise incisions in the cornea, in the lens capsule, and/or in the crystalline lens nucleus. The system 2 includes a main unit 4, a patient chair 6, a dual function footswitch 8, and a laser footswitch 10.

The main unit 4 includes many primary subsystems of the system 2. For example, externally visible subsystems include a touch-screen control panel 12, a patient interface assembly 14, patient interface vacuum connections 16, a docking control keypad 18, a patient interface radio frequency identification (RFID) reader 20, external connections 22 (e.g., network, video output, footswitch, USB port, door interlock, and AC power), laser emission indicator 24, emergency laser stop button 26, key switch 28, and USB data ports 30.

The patient chair 6 includes a base 32, a patient support bed 34, a headrest 36, a positioning mechanism, and a patient chair joystick control 38 disposed on the headrest 36. The positioning control mechanism is coupled between the base 32 and the patient support bed 34 and headrest 36. The patient chair 6 is configured to be adjusted and oriented in three axes (x, y, and z) using the patient chair joystick control 38. The headrest 36 and a restrain system (not shown, e.g., a restraint strap engaging the patient's forehead) stabilize the patient's head during the procedure. The headrest 36 includes an adjustable neck support to provide patient comfort and to reduce patient head movement. The headrest 36 is configured to be vertically adjustable to enable adjustment of the patient head position to provide patient comfort and to accommodate variation in patient head size.

The patient chair 6 allows for tilt articulation of the patient's legs, torso, and head using manual adjustments. The patient chair 6 accommodates a patient load position, a suction ring capture position, and a patient treat position. In the patient load position, the chair 6 is rotated out from under the main unit 4 with the patient chair back in an upright position and patient footrest in a lowered position. In the suction ring capture position, the chair is rotated out from under the main unit 4 with the patient chair back in reclined position and patient footrest in raised position. In the patient treat position, the chair is rotated under the main unit 4 with the patient chair back in reclined position and patient footrest in raised position.

The patient chair 6 is equipped with a "chair enable" feature to protect against unintended chair motion. The patient chair joystick 38 can be enabled in either of two ways. First, the patient chair joystick 38 incorporates a "chair enable" button located on the top of the joystick. Control of the position of the patient chair 6 via the joystick 38 can be enabled by continuously pressing the "chair enable" button. Alternately, the left foot switch 40 of the dual function footswitch 8 can be continuously depressed to enable positional control of the patient chair 6 via the joystick 38.

In many embodiments, the patient control joystick 38 is a proportional controller. For example, moving the joystick a small amount can be used to cause the chair to move slowly. Moving the joystick a large amount can be used to cause the chair to move faster. Holding the joystick at its maximum travel limit can be used to cause the chair to move at the maximum chair speed. The available chair speed can be reduced as the patient approaches the patient interface assembly 14.

The emergency stop button 26 can be pushed to stop emission of all laser output, release vacuum that couples the patient to the system 2, and disable the patient chair 6. The stop button 26 is located on the system front panel, next to the key switch 28.

The key switch 28 can be used to enable the system 2. When in a standby position, the key can be removed and the system is disabled. When in a ready position, the key enables power to the system 2.

The dual function footswitch 8 is a dual footswitch assembly that includes the left foot switch 40 and a right foot switch 42. The left foot switch 40 is the "chair enable" footswitch. The right footswitch 42 is a "vacuum ON" footswitch that enables vacuum to secure a liquid optics interface suction ring to the patient's eye. The laser footswitch 10 is a shrouded footswitch that activates the treatment laser when depressed while the system is enabled.

In many embodiments, the system 2 includes external communication connections. For example, the system 2 can include a network connection (e.g., an RJ45 network connection) for connecting the system 2 to a network. The network connection can be used to enable network printing of treatment reports, remote access to view system performance logs, and remote access to perform system diagnostics. The system 2 can include a video output port (e.g., HDMI) that can be used to output video of treatments performed by the system 2. The output video can be displayed on an external monitor for, for example, viewing by family members and/or training. The output video can also be recorded for, for example, archival purposes. The system 2 can include one or more data output ports (e.g., USB) to, for example, enable export of treatment reports to a data storage device. The treatments reports stored on the data storage device can then be accessed at a later time for any suitable purpose such as, for example, printing from an external computer in the case where the user without access to network based printing.

Figure 3:
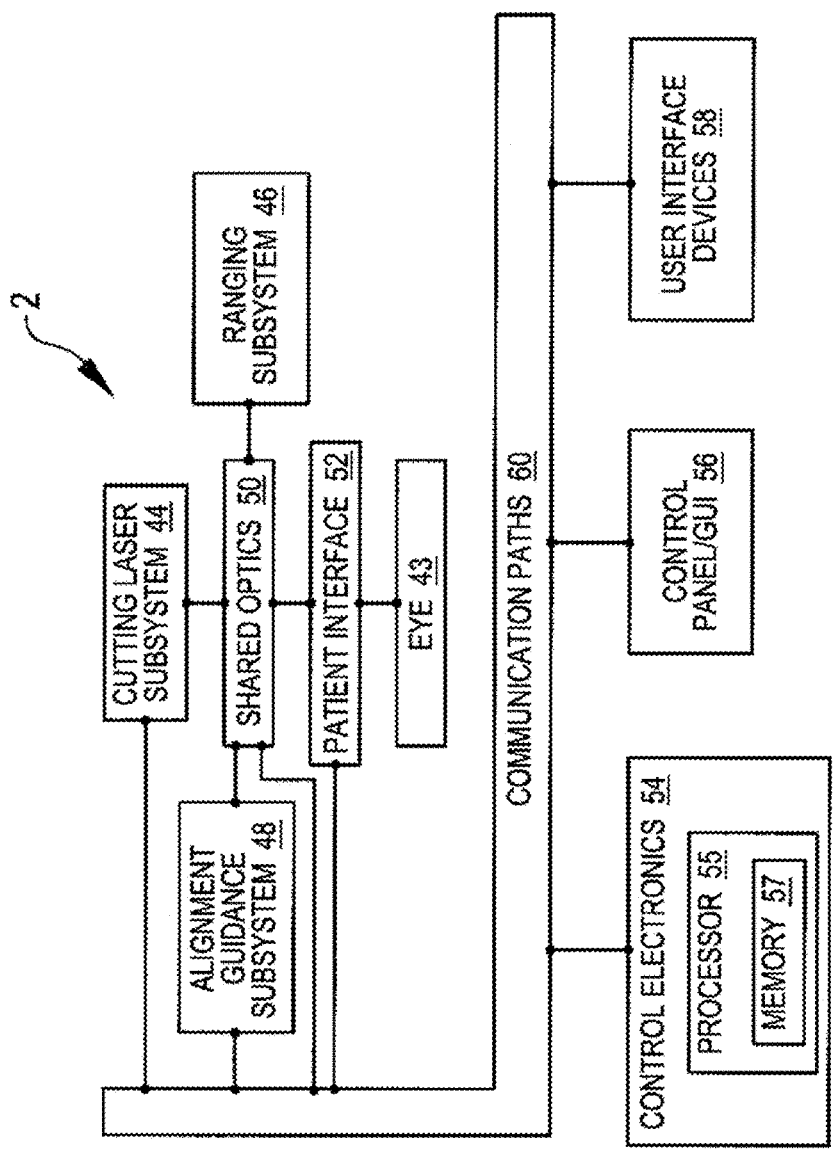
FIG. 3 shows a simplified block diagram of the system of FIG. 2 coupled with a patient eye.

FIG. 3 shows a simplified block diagram of the system 2 coupled with a patient eye 43. The patient eye 43 comprises a cornea 43C, a lens 43L and an iris 43I. The iris 43I defines a pupil of the eye 43 that may be used for alignment of eye 43 with system 2. The system 2 includes a cutting laser subsystem 44, a ranging subsystem 46, an alignment guidance system 48, shared optics 50, a patient interface 52, control electronics 54, a control panel/GUI 56, user interface devices 58, and communication paths 60. The control electronics 54 is operatively coupled via the communication paths 60 with the cutting laser subsystem 44, the ranging subsystem 46, the alignment guidance subsystem 48, the shared optics 50, the patient interface 52, the control panel/GUI 56, and the user interface devices 58.

In some embodiments, the cutting laser subsystem 44 incorporates femtosecond (FS) laser technology. By using femtosecond laser technology, a short duration (e.g., approximately $10^{13}$ seconds in duration) laser pulse (with energy level in the micro joule range) can be delivered to a tightly focused point to disrupt tissue, thereby substantially lowering the energy level required as compared to the level required for ultrasound fragmentation of the lens nucleus and as compared to laser pulses having longer durations. In other embodiments, a pulse duration of the laser pulses is generally between 1 ps and 100 ns.

The cutting laser subsystem 44 can produce laser pulses having a wavelength suitable to the configuration of the system 2. As a non-limiting example, the system 2 can be configured, in a first embodiment, to use a cutting laser subsystem 44 that produces laser pulses having a wavelength from 1020 nm to 1050 nm. For example, the cutting laser subsystem 44 can have a diode-pumped solid-state configuration with a 1030 (+/−5) nm center wavelength.

In a second embodiment, the system 2 can be configured with a cutting laser subsystem 44 that produces ultraviolet laser pulses. More specifically, the ultraviolet light pulses generally have a wavelength of between 320 nm and 430 nm, preferably between 320 and 400 nm, preferably between 320 to 370 nm, and more preferably between 340 nm and 360 nm. In many embodiments, the laser pulses have a wavelength of 355 nm. The 320 nm to 430 nm light source may be, for instance, a Nd:YAG laser source operating at the 3rd harmonic wavelength, 355 nm.

When an ultraviolet wavelength is used, the pulse energy of laser pulses is generally between 0.01 µJ and 500 µJ. In many embodiments, the pulse energy will be between 0.1 µJ and 100 µJ, or more precisely, between 0.1 µJ and 40µJ, or between 0.1 µJ and 10 µJ.

When an ultraviolet wavelength is used, a pulse repetition rate of the laser pulses is generally between 500 Hz and 500 kHz. In many embodiments, the pulse repetition rate is between 1 kHz to 200 kHz, or between 1 KHz to 100 KHz.

When an ultraviolet wavelength is used, spot sizes of the laser pulses are generally smaller than 10 µm. In many embodiments, the spot size is preferably smaller than 5 µm, typically 0.5 µm to 3 µm.

When an ultraviolet wavelength is used, a pulse duration of the laser pulses is generally between 1 ps and 100 ns. In many embodiments, the pulse duration is between 100 ps to 10 ns, or between 100 ps and 1 ns. In a preferred embodiment, the pulse duration is between 300 ps and 700 ps, preferably 400 ps to 700 ps.

In some embodiments when an ultraviolet wavelength is used, the beam quality, also referred to as $M^2$ factor, is between 1 and 1.3. The $M^2$ factor is a common measure of the beam quality of a laser beam. In brief, the $M^2$ factor is defined as the ratio of a beam's actual divergence to the divergence of an ideal, diffraction limited, Gaussian TEM00 beam having the same waist size and location as is described in ISO Standard 11146.

In some embodiments when an ultraviolet wavelength is used, a peak power density, obtained by dividing the peak power of the laser pulse by the focal spot size, is generally expressed in units of GW/cm2. In general, the peak power density of the laser pulses should be sufficiently high to modify the ocular tissue to be treated. As would be understood by those ordinarily skilled, the peak power density depends upon a number of factors, including the wavelength of the selected laser pulses. In some embodiments, a peak power density is generally in the range of 100 GW/cm$^2$ to 800 GW/cm$^2$ will be used to cut ocular tissue with 355 nm light.

In some embodiments when an ultraviolet wavelength is used, the scan range of the laser surgical system is preferably in the range of 6 to 10 mm.

In some embodiments when an ultraviolet wavelength is used, spot spacing between adjacent laser pulses is typically in the range of about 0.20 µm to 10 µm, preferably 0.2 µm to 6 µm.

In some embodiments when an ultraviolet wavelength is used, a numerical aperture should be selected that preferably provides for the focal spot of the laser beam to be scanned over a scan range of 6 mm to 10 mm in a direction lateral to a Z-axis that is aligned with the laser beam. The NA of the system should be less than 0.6, preferably less than 0.5 and more preferably in a range of 0.05 to 0.4, typically between 0.1 and 0.3. In some specific embodiments, the NA is 0.15. For each selected NA, there are suitable ranges of pulse energy and beam quality (measured as an $M^2$ value) necessary to achieve a peak power density in the range required to cut the ocular tissue. Further considerations when choosing the NA include available laser power and pulse rate, and the time needed to make a cut. Further, in selection of an appropriate NA, it is preferable to ensure that there is a safe incidental exposure of the iris, and other ocular tissues, that are not targeted for cuts.

When UV wavelengths are used, the tissue modification is carried out using chromophore absorption without plasma formation and/or without bubble formation and an associated cavitation event. Here, chromophore absorption refers to the absorption of at least a portion of the ultraviolet light by one or more chemical species in the target area. The use of ultraviolet light significantly reduces the threshold for plasma formation and associated formation of cavitation bubbles but also decreases the threshold energy required for linear absorption enhanced photodecomposition without the formation of cavitation bubbles for a few reasons. First, the focused spot diameter scales linearly with wavelength which squares the peak radiant exposure within the focal plane. Second, the linear absorption of the material itself allows an even lower threshold for plasma formation or low density photodecomposition as initially more laser energy is absorbed in the target structure. Third, the use of UV laser pulses in the nanosecond and sub-nanosecond regime enables linear absorption enhanced photodecomposition and chromophore guided ionization.

Furthermore, this chromophore guided ionization when using ultraviolet wavelength strongly lowers the threshold for ionization in case of plasma formation as well lowers the threshold for low density photodecomposition for material modification or alteration without cavitation even under very weak absorption. The linear absorption also allows for the specific treatment of topical lens structures (e.g. the lens capsule) as the optical penetration depth of the laser beam is limited by the linear absorption of the lens. This is especially true for aged lenses which absorption in the UV-blue spectral region increases strongly compared to young lenses.

The cutting laser subsystem 44 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly to adapt the beam containing the laser pulses to the characteristics of the system 2 and a fixed optical relay to transfer the laser pulses over a distance while accommodating laser pulse beam positional and/or directional variability, thereby providing increased tolerance for component variation.

The ranging subsystem 46 is configured to measure the spatial disposition of eye structures in three dimensions. The measured eye structures can include the anterior and posterior surfaces of the cornea, the anterior and posterior portions of the lens capsule, the iris, and the limbus. In many embodiments, the ranging subsystem 46 utilizes optical coherence tomography (OCT) imaging. As a non-limiting example, the system 2 can be configured to use an OCT imaging system employing wavelengths from 780 nm to 970 nm. For example, the ranging subsystem 46 can include an OCT imaging system that employs a broad spectrum of wavelengths from 810 nm to 850 nm. Such an OCT imaging system can employ a reference path length that is adjustable to adjust the effective depth in the eye of the OCT measurement, thereby allowing the measurement of system components including features of the patient interface that lie anterior to the cornea of the eye and structures of the eye that range in depth from the anterior surface of the cornea to the posterior portion of the lens capsule and beyond.

The alignment guidance subsystem 48 can include a laser diode or gas laser that produces a laser beam used to align optical components of the system 2. The alignment guidance subsystem 48 can include LEDs or lasers that produce a fixation light to assist in aligning and stabilising the patient's eye during docking and treatment. The alignment guidance subsystem 48 can include a laser or LED light source and a detector to monitor the alignment and stability of the actuators used to position the beam in X, Y, and Z. The alignment guidance subsystem 48 can include a video system that can be used to provide imaging of the patient's eye to facilitate docking of the patient's eye 43 to the patient interface 52. The imaging system provided by the video system can also be used to direct via the GUI the location of cuts. The imaging provided by the video system can additionally be used during the laser eye surgery procedure to monitor the progress of the procedure, to track movements of the patient's eye 43 during the procedure, and to measure the location and size of structures of the eye such as the pupil and/or limbus.

The shared optics 50 provides a common propagation path that is disposed between the patient interface 52 and each of the cutting laser subsystem 44, the ranging subsystem 46, and the alignment guidance subsystem 48. In many embodiments, the shared optics 50 includes beam combiners to receive the emission from the respective subsystem (e.g., the cutting laser subsystem 44, and the alignment guidance subsystem 48) and redirect the emission along the common propagation path to the patient interface. In many embodiments, the shared optics 50 includes an objective lens assembly that focuses each laser pulse into a focal point. In many embodiments, the shared optics 50 includes scanning mechanisms operable to scan the respective emission in three dimensions. For example, the shared optics can include an XY-scan mechanism(s) and a Z-scan mechanism. The XY-scan mechanism(s) can be used to scan the respective emission in two dimensions transverse to the propagation direction of the respective emission. The Z-scan mechanism can be used to vary the depth of the focal point within the eye 43. In many embodiments, the scanning mechanisms are disposed between the laser diode and the objective lens such that the scanning mechanisms are used to scan the alignment laser beam produced by the laser diode. In contrast, in many embodiments, the video system is disposed between the scanning mechanisms and the objective lens such that the scanning mechanisms do not affect the image obtained by the video system.

The patient interface 52 is used to restrain the position of the patient's eye 43 relative to the system 2. In many embodiments, the patient interface 52 employs a suction ring that is vacuum attached to the patient's eye 43. The suction ring is then coupled with the patient interface 52, for example, using vacuum to secure the suction ring to the patient interface 52. In many embodiments, the patient interface 52 includes an optically transmissive structure having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the patient interface lens posterior surface and the patient's cornea and forms part of a transmission path between the shared optics 50 and the patient's eye 43. The optically transmissive structure may comprise a lens 96 having one or more curved surfaces. Alternatively, the patient interface 22 may comprise an optically transmissive structure having one or more substantially flat surfaces such as a parallel plate or wedge. In many embodiments, the patient interface lens is disposable and can be replaced at any suitable interval, such as before each eye treatment.

The control electronics 54 controls the operation of and can receive input from the cutting laser subsystem 44, the ranging subsystem 46, the alignment guidance subsystem 48, the patient interface 52, the control panel/GUI 56, and the user interface devices 58 via the communication paths 60. The communication paths 60 can be implemented in any suitable configuration, including any suitable shared or dedicated communication paths between the control electronics 54 and the respective system components. The control electronics 54 can include any suitable components, such as one or more processors 55, one or more field-programmable gate arrays (FPGA), and one or more memory storage devices 57. In many embodiments, the control electronics 54 controls the control panel/GUI 56 to provide for pre-procedure planning according to user specified treatment parameters as well as to provide user control over the laser eye surgery procedure or to display image data to the user.

The user interface devices 58 can include any suitable user input device suitable to provide user input to the control electronics 54. For example, the user interface devices 58 can include devices such as, for example, the dual function footswitch 8, the laser footswitch 10, the docking control keypad 18, the patient interface radio frequency identification (RFID) reader 20, the emergency laser stop button 26, the key switch 28, and the patient chair joystick control 38.

Figure 4:
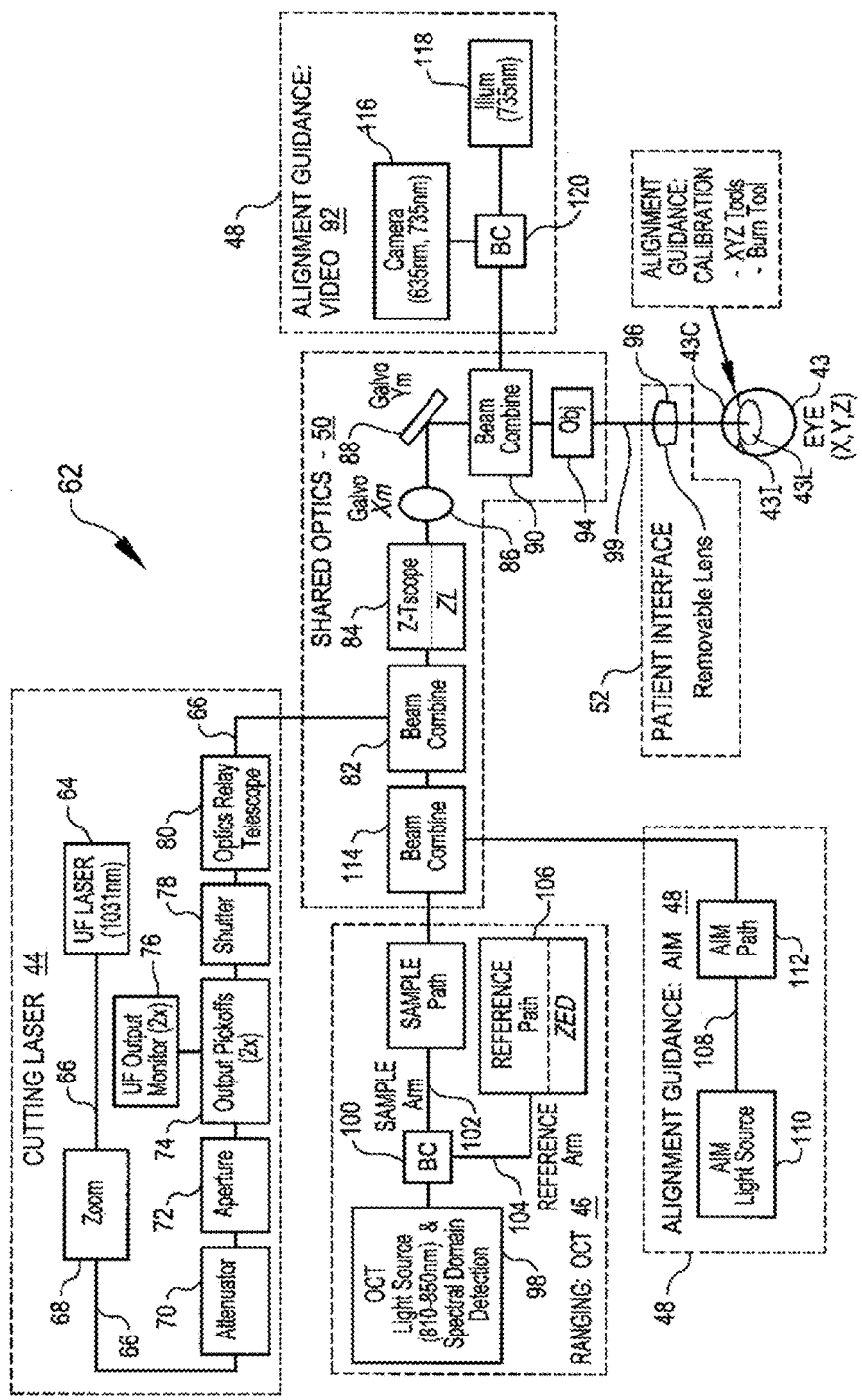
FIG. 4 is a simplified block diagram illustrating an assembly in accordance with many embodiments that can be included in the system of FIG. 2.

FIG. 4 is a simplified block diagram illustrating an assembly 62, in accordance with many embodiments, that can be included in the system 2. The assembly 62 is a non-limiting example of suitable configurations and integration of the cutting laser subsystem 44, the ranging subsystem 46, the alignment guidance subsystem 48, the shared optics 50, and the patient interface 52. Other configurations and integration of the cutting laser subsystem 44, the ranging subsystem 46, the alignment guidance subsystem 48, the shared optics 50, and the patient interface 52 may be possible and may be apparent to a person of skill in the art.

The assembly 62 is operable to project and scan optical beams into the patient's eye 43. The cutting laser subsystem 44 includes a laser 64. Using the assembly 62, optical beams can be scanned in the patient's eye 43 in three dimensions: X, Y, Z. For example, short-pulsed laser light generated by the laser 64 can be focused into eye tissue to produce dielectric breakdown to cause photodisruption around the focal point (the focal zone), thereby rupturing the tissue in the vicinity of the photo-induced plasma. In one embodiment of the assembly 62, the wavelength of the laser light can vary between 800 nm to 1200 nm and the pulse width of the laser light can vary from 10 fs to 10000 fs. The pulse repetition frequency can also vary from 10 kHz to 500 kHz. Safety limits with regard to unintended damage to non-targeted tissue bound the upper limit with regard to repetition rate and pulse energy. Threshold energy, time to complete the procedure, and stability can bound the lower limit for pulse energy and repetition rate. The peak power of the focused spot in the eye 43 and specifically within the crystalline lens and the lens capsule of the eye is sufficient to produce optical breakdown and initiate a plasma-mediated ablation process. Near-infrared wavelengths for the laser light are preferred because linear optical absorption and scattering in biological tissue is reduced for near-infrared wavelengths. As an example, the laser 64 can be a repetitively pulsed 1031 nm device that produces pulses with less than 600 fs duration at a repetition rate of 120 kHz (+/−5%) and individual pulse energy in the 1 to 20 micro joule range.

In another embodiment, the assembly 62 is operable to project and scan an ultraviolet optical beam into the patient's eye 43. The cutting laser subsystem 44 includes a laser 64 that produces ultraviolet laser pulses having a wavelength of between 320 nm and 430 nm, a pulse duration between about 1 picosecond and 100 nanoseconds, and the pulse energy of laser pulses is generally between 0.01 µJ and 500 µJ. In many embodiments, the pulse energy will be between 0.1 µJ and 100 µJ, or more precisely, between 0.1 µJ and 40 µJ, or between 0.1 µJ and and a pulse duration of the laser pulses is generally between 1 ps and 100 ns.

The cutting laser subsystem 44 is controlled by the control electronics 54 and the user, via the control panel/GUI 56 and the user interface devices 58, to create a laser pulse beam 66. The control panel/GUI 56 is used to set system operating parameters, process user input, display gathered information such as images of ocular structures, and display representations of incisions to be formed in the patient's eye 43.

The generated laser pulse beam 66 proceeds through a zoom assembly 68. The laser pulse beam 66 may vary from unit to unit, particularly when the laser 64 may be obtained from different laser manufacturers. For example, the beam diameter of the laser pulse beam 66 may vary from unit to unit (e.g., by +/−20%). The beam may also vary with regard to beam quality, beam divergence, beam spatial circularity, and astigmatism. In many embodiments, the zoom assembly 68 is adjustable such that the laser pulse beam 66 exiting the zoom assembly 68 has consistent beam diameter and divergence unit to unit.

After exiting the zoom assembly 68, the laser pulse beam 66 proceeds through an attenuator 70. The attenuator 70 is used to adjust the transmission of the laser beam and thereby the energy level of the laser pulses in the laser pulse beam 66. The attenuator 70 is controlled via the control electronics 54.

After exiting the attenuator 70, the laser pulse beam 66 proceeds through an aperture 72. The aperture 72 sets the outer useful diameter of the laser pulse beam 66. In turn, the zoom determines the size of the beam at the aperture location and therefore the amount of light that is transmitted. The amount of transmitted light is bounded both high and low. The upper is bounded by the requirement to achieve the highest numerical aperture achievable in the eye. High NA promotes low threshold energies and greater safety margin for untargeted tissue. The lower is bound by the requirement for high optical throughput. Too much transmission loss in the system shortens the lifetime of the system as the laser output and system degrades over time. Additionally, consistency in the transmission through this aperture promotes stability in determining optimum settings (and sharing of) for each procedure. Typically to achieve optimal performance the transmission through this aperture as set to be between 88% to 92%.

After exiting the aperture 72, the laser pulse beam 66 proceeds through two output pickoffs 74. Each output pickoff 74 can include a partially reflecting mirror to divert a portion of each laser pulse to a respective output monitor 76. Two output pickoffs 74 (e.g., a primary and a secondary) and respective primary and secondary output monitors 76 are used to provide redundancy in case of malfunction of the primary output monitor 76.

After exiting the output pickoffs 74, the laser pulse beam 66 proceeds through a system-controlled shutter 78. The system-controlled shutter 78 ensures on/off control of the laser pulse beam 66 for procedural and safety reasons. The two output pickoffs precede the shutter allowing for monitoring of the beam power, energy, and repetition rate as a pre-requisite for opening the shutter.

After exiting the system-controlled shutter 78, the optical beam proceeds through an optics relay telescope 80. The optics relay telescope 80 propagates the laser pulse beam 66 over a distance while accommodating positional and/or directional variability of the laser pulse beam 66, thereby providing increased tolerance for component variation. As an example, the optical relay can be a keplerian afocal telescope that relays an image of the aperture position to a conjugate position near to the XY galvo mirror positions. In this way, the position of the beam at the XY galvo location is invariant to changes in the beams angle at the aperture position. Similarly the shutter does not have to precede the relay and may follow after or be included within the relay.

After exiting the optics relay telescope 80, the laser pulse beam 66 is transmitted to the shared optics 50, which propagates the laser pulse beam 66 to the patient interface 52. The laser pulse beam 66 is incident upon a beam combiner 82, which reflects the laser pulse beam 66 while transmitting optical beams from the ranging subsystem 46 and the alignment guidance subsystem: AIM 48.

Following the beam combiner 82, the laser pulse beam 66 continues through a Z-telescope 84, which is operable to scan focus position of the laser pulse beam 66 in the patient's eye 43 along the Z axis. For example, the Z-telescope 84 can include a Galilean telescope with two lens groups (each lens group includes one or more lenses). One of the lens groups moves along the Z axis about the collimation position of the Z-telescope 84. In this way, the focus position of the spot in the patient's eye 43 moves along the Z axis. In general, there is a relationship between the motion of lens group and the motion of the focus point. For example, the Z-telescope can have an approximate 2× beam expansion ratio and close to a 1:1 relationship of the movement of the lens group to the movement of the focus point. The exact relationship between the motion of the lens and the motion of the focus in the z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. The Z-telescope 84 functions as z-scan device for scanning the focus point of the laser-pulse beam 66 in the patient's eye 43. The Z-telescope 84 can be controlled automatically and dynamically by the control electronics 54 and selected to be independent or to interplay with the X and Y scan devices described next.

After passing through the Z-telescope 84, the laser pulse beam 66 is incident upon an X-scan device 86, which is operable to scan the laser pulse beam 66 in the X direction, which is dominantly transverse to the Z axis and transverse to the direction of propagation of the laser pulse beam 66. The X-scan device 86 is controlled by the control electronics 54, and can include suitable components, such as a motor, galvanometer, or any other well-known optic moving device. The relationship of the motion of the beam as a function of the motion of the X actuator does not have to be fixed or linear. Modeling or calibrated measurement of the relationship or a combination of both can be determined and used to direct the location of the beam.

After being directed by the X-scan device 86, the laser pulse beam 66 is incident upon a Y-scan device 88, which is operable to scan the laser pulse beam 66 in the Y direction, which is dominantly transverse to the X and Z axes. The Y-scan device 88 is controlled by the control electronics 54, and can include suitable components, such as a motor, galvanometer, or any other well-known optic moving device. The relationship of the motion of the beam as a function of the motion of the Y actuator does not have to be fixed or linear. Modeling or calibrated measurement of the relationship or a combination of both can be determined and used to direct the location of the beam. Alternatively, the functionality of the X-Scan device 86 and the Y-Scan device 88 can be provided by an XY-scan device configured to scan the laser pulse beam 66 in two dimensions transverse to the Z axis and the propagation direction of the laser pulse beam 66. The X-scan and Y-scan devices 86, 88 change the resulting direction of the laser pulse beam 66, causing lateral displacements of the focus point located in the patient's eye 43.

After being directed by the Y-scan device 88, the laser pulse beam 66 passes through a beam combiner 90. The beam combiner 90 is configured to transmit the laser pulse beam 66 while reflecting optical beams to and from a video subsystem 92 of the alignment guidance subsystem 48.

After passing through the beam combiner 90, the laser pulse beam 66 passes through an objective lens assembly 94. The objective lens assembly 94 can include one or more lenses. In many embodiments, the objective lens assembly 94 includes multiple lenses. The complexity of the objective lens assembly 94 may be driven by the scan field size, the focused spot size, the degree of telecentricity, the available working distance on both the proximal and distal sides of objective lens assembly 94, as well as the amount of aberration control.

After passing through the objective lens assembly 94, the laser pulse beam 66 passes through the patient interface 52. As described above, in many embodiments, the patient interface 52 includes a patient interface lens 96 having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the posterior surface of the patient interface lens 96 and the patient's cornea and forms part of an optical transmission path between the shared optics 50 and the patient's eye 43.

The shared optics 50 under the control of the control electronics 54 can automatically generate aiming, ranging, and treatment scan patterns. Such patterns can be comprised of a single spot of light, multiple spots of light, a continuous pattern of light, multiple continuous patterns of light, and/or any combination of these. In addition, the aiming pattern (using the aim beam 108 described below) need not be identical to the treatment pattern (using the laser pulse beam 66), but can optionally be used to designate the boundaries of the treatment pattern to provide verification that the laser pulse beam 66 will be delivered only within the desired target area for patient safety. This can be done, for example, by having the aiming pattern provide an outline of the intended treatment pattern. This way the spatial extent of the treatment pattern can be made known to the user, if not the exact locations of the individual spots themselves, and the scanning thus optimized for speed, efficiency, and/or accuracy. The aiming pattern can also be made to be perceived as blinking in order to further enhance its visibility to the user. Likewise, the ranging beam 102 need not be identical to the treatment beam or pattern. The ranging beam needs only to be sufficient enough to identify targeted surfaces. These surfaces can include the cornea and the anterior and posterior surfaces of the lens and may be considered spheres with a single radius of curvature. Also the optics shared by the alignment guidance: video subsystem does not have to be identical to those shared by the treatment beam. The positioning and character of the laser pulse beam 66 and/or the scan pattern the laser pulse beam 66 forms on the eye 43 may be further controlled by use of an input device such as a joystick, or any other appropriate user input device (e.g., control panel/GUI 56) to position the patient and/or the optical system.

The control electronics 54 can be configured to target the targeted structures in the eye 43 and ensure that the laser pulse beam 66 will be focused where appropriate and not unintentionally damage non-targeted tissue. Imaging modalities and techniques described herein, such as those mentioned above, or ultrasound may be used to determine the location and measure the thickness of the lens and lens capsule to provide greater precision to the laser focusing methods, including 2D and 3D patterning. Laser focusing may also be accomplished by using one or more methods including direct observation of an aiming beam, or other known ophthalmic or medical imaging modalities, such as those mentioned above, and/or combinations thereof. Additionally the ranging subsystem such as an OCT can be used to detect features or aspects involved with the patient interface. Features can include fiducials places on the docking structures and optical structures of the disposable lens such as the location of the anterior and posterior surfaces.

In the embodiment of FIG. 4, the ranging subsystem 46 includes an OCT imaging device. Additionally or alternatively, imaging modalities other than OCT imaging can be used. An OCT scan of the eye can be used to measure the spatial disposition (e.g., three dimensional coordinates such as X Y, and Z of points on boundaries) of structures of interest in the patient's eye 43. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, and/or the limbus. The spatial disposition of the structures of interest and/or of suitable matching geometric modeling such as surfaces and curves can be generated and/or used by the control electronics 54 to program and control the subsequent laser-assisted surgical procedure. The spatial disposition of the structures of interest and/or of suitable matching geometric modeling can also be used to determine a wide variety of parameters related to the procedure such as, for example, the upper and lower axial limits of the focal planes used for cutting the lens capsule and segmentation of the lens cortex and nucleus, and the thickness of the lens capsule among others.

It should be also noted that laser pulse beam 66 may also be attenuated to the nanoJoule level and used instead of the OCT system described above and used for imaging of the target structure. Such a configuration provides for the most direct correlation between the position of the focal locations for imaging and treatment—they are the same beam. This attenuated probe beam can be used directly in a back reflectance measuring configuration, or even indirectly in a fluorescence detection scheme. Since you will see increases in both backscatter and fluorescence within tissue structures, both approaches have merit. They may also be utilized to deliver a sparse pattern in order to limit the patient's exposure, while still discerning a reasonable map of the intraocular targets.

The ranging subsystem 46 in FIG. 4 includes an OCT light source and detection device 98. The OCT light source and detection device 98 includes a light source that generates and emits light with a suitable broad spectrum. For example, in many embodiments, the OCT light source and detection device 98 generates and emits light with a broad spectrum from 810 nm to 850 nm wavelength. The generated and emitted light is coupled to the device 98 by a single mode fiber optic connection.

The light emitted from the OCT light source and detection device 98 is passed through a beam combiner 100, which divides the light into a sample portion 102 and a reference portion 104. A significant portion of the sample portion 102 is transmitted through the shared optics 50. A relative small portion of the sample portion is reflected from the patient interface 52 and/or the patient's eye 43 and travels back through the shared optics 50, back through the beam combiner 100 and into the OCT light source and detection device 98. The reference portion 104 is transmitted along a reference path 106 having an adjustable path length. The reference path 106 is configured to receive the reference portion 104 from the beam combiner 100, propagate the reference portion 104 over an adjustable path length, and then return the reference portion 106 back to the beam combiner 100, which then directs the returned reference portion 104 back to the OCT light source and detection device 98. The OCT light source and detection device 98 then directs the returning small portion of the sample portion 102 and the returning reference portion 104 into a detection assembly, which employs a time domain detection technique, a frequency detection technique, or a single point detection technique. For example, a frequency-domain technique can be used with an OCT wavelength of 830 nm and bandwidth of 10 nm.

Once combined with the laser pulse beam 66 subsequent to the beam combiner 82, the OCT sample portion beam 102 follows a shared path with the laser pulse beam 66 through the shared optics 50 and the patient interface 52. In this way, the OCT sample portion beam 102 is generally indicative of the location of the laser pulse beam 66. Similar to the laser beam, the OCT sample portion beam 102 passes through the Z-telescope 84, is redirected by the X-scan device 86 and by the Y-scan device 88, passes through the objective lens assembly 94 and the patient interface 52, and on into the eye 43. Reflections and scatter off of structures within the eye provide return beams that retrace back through the patient interface 52, back through the shared optics 50, back through the beam combiner 100, and back into the OCT light source and detection device 98. The returning back reflections of the sample portion 102 are combined with the returning reference portion 104 and directed into the detector portion of the OCT light source and detection device 98, which generates OCT signals in response to the combined returning beams. The generated OCT signals that are in turn interpreted by the control electronics to determine the spatial disposition of the structures of interest in the patient's eye 43. The generated OCT signals can also be interpreted by the control electronics to measure the position and orientation of the patient interface 52, as well as to determine whether there is liquid disposed between the posterior surface of the patient interface lens 96 and the patient's eye 43.

The OCT light source and detection device 98 works on the principle of measuring differences in optical path length between the reference path 106 and the sample path. Therefore, different settings of the Z-tele scope 84 to change the focus of the laser beam do not impact the length of the sample path for a axially stationary surface in the eye of patient interface volume because the optical path length does not change as a function of different settings of the Z-tele scope 84. The ranging subsystem 46 has an inherent Z range that is related to light source and the detection scheme, and in the case of frequency domain detection the Z range is specifically related to the spectrometer, the wavelength, the bandwidth, and the length of the reference path 106. In the case of ranging subsystem 46 used in FIG. 4, the Z range is approximately 4-5 mm in an aqueous environment. Extending this range to at least 20-25 mm involves the adjustment of the path length of the reference path 106 via a stage ZED within ranging subsystem 46. Passing the OCT sample portion beam 102 through the Z-telescope 84, while not impacting the sample path length, allows for optimization of the OCT signal strength. This is accomplished by focusing the OCT sample portion beam 102 onto the targeted structure. The focused beam both increases the return reflected or scattered signal that can be transmitted through the single mode fiber and increases the spatial resolution due to the reduced extent of the focused beam. The changing of the focus of the sample OCT beam can be accomplished independently of changing the path length of the reference path 106.

Because of the fundamental differences in how the sample portion 102 (e.g., 810 nm to 850 nm wavelengths) and the laser pulse beam 66 (e.g., 1020 nm to 1050 nm wavelengths) propagate through the shared optics 50 and the patient interface 52 due to influences such as immersion index, refraction, and aberration, both chromatic and monochromatic, care must be taken in analyzing the OCT signal with respect to the laser pulse beam 66 focal location. A calibration or registration procedure as a function of X Y, and Z can be conducted in order to match the OCT signal information to the laser pulse beam focus location and also to the relative to absolute dimensional quantities.

There are many suitable possibilities for the configuration of the OCT interferometer. For example, alternative suitable configurations include time and frequency domain approaches, single and dual beam methods, swept source, etc., are described in U.S. Pat. Nos. 5,748,898; 5,748,352; 5,459,570; 6,111,645; and 6,053,613.

The system 2 can be set to locate the anterior and posterior surfaces of the lens capsule and cornea and ensure that the laser pulse beam 66 will be focused on the lens capsule and cornea at all points of the desired opening. Imaging modalities and techniques described herein, such as for example, Optical Coherence Tomography (OCT), and such as Purkinje imaging, Scheimpflug imaging, confocal or non-linear optical microscopy, fluorescence imaging, ultrasound, structured light, stereo imaging, or other known ophthalmic or medical imaging modalities and/or combinations thereof may be used to determine the shape, geometry, perimeter, boundaries, and/or 3-dimensional location of the lens and lens capsule and cornea to provide greater precision to the laser focusing methods, including 2D and 3D patterning. Laser focusing may also be accomplished using one or more methods including direct observation of an aiming beam, or other known ophthalmic or medical imaging modalities and combinations thereof, such as but not limited to those defined above.

Optical imaging of the cornea, anterior chamber and lens can be performed using the same laser and/or the same scanner used to produce the patterns for cutting. Optical imaging can be used to provide information about the axial location and shape (and even thickness) of the anterior and posterior lens capsule, the boundaries of the cataract nucleus, as well as the depth of the anterior chamber and features of the cornea. This information may then be loaded into the laser 3-D scanning system or used to generate a three dimensional model/representation/image of the cornea, anterior chamber, and lens of the eye, and used to define the cutting patterns used in the surgical procedure.

Observation of an aim beam can also be used to assist in positioning the focus point of the laser pulse beam 66. Additionally, an aim beam visible to the unaided eye in lieu of the infrared OCT sample portion beam 102 and the laser pulse beam 66 can be helpful with alignment provided the aim beam accurately represents the infrared beam parameters. The alignment guidance subsystem 48 is included in the assembly 62 shown in FIG. 4. An aim beam 108 is generated by an aim beam light source 110, such as a laser diode in the 630-650 nm range.

Once the aim beam light source 110 generates the aim beam 108, the aim beam 108 is transmitted along an aim path 112 to the shared optics 50, where it is redirected by a beam combiner 114. After being redirected by the beam combiner 114, the aim beam 108 follows a shared path with the laser pulse beam 66 through the shared optics 50 and the patient interface 52. In this way, the aim beam 108 is indicative of the location of the laser pulse beam 66. The aim beam 108 passes through the Z-telescope 84, is redirected by the X-scan device 86 and by the Y-scan device 88, passes through the beam combiner 90, passes through the objective lens assembly 94 and the patient interface 52, and on into the patient's eye 43.

The video subsystem 92 is operable to obtain images of the patient interface and the patient's eye. The video subsystem 92 includes a camera 116, an illumination light source 118, and a beam combiner 120. The video subsystem 92 gathers images that can be used by the control electronics 54 for providing pattern centering about or within a predefined structure. The illumination light source 118 can be generally broadband and incoherent. For example, the light source 118 can include multiple LEDs. The wavelength of the illumination light source 118 is preferably in the range of 700 nm to 750 nm, but can be anything that is accommodated by the beam combiner 90, which combines the light from the illumination light source 118 with the beam path for the laser pulse beam 66, the OCT sample beam 102, and the aim beam 108 (beam combiner 90 reflects the video wavelengths while transmitting the OCT and cutting laser wavelengths). The beam combiner 90 may partially transmit the aim beam 108 wavelength so that the aim beam 108 can be visible to the camera 116. An optional polarization element can be disposed in front of the illumination light source 118 and used to optimize signal. The optional polarization element can be, for example, a linear polarizer, a quarter wave plate, a half-wave plate or any combination. An additional optional analyzer can be placed in front of the camera. The polarizer analyzer combination can be crossed linear polarizers thereby eliminating specular reflections from unwanted surfaces such as the objective lens surfaces while allowing passage of scattered light from targeted surfaces such as the intended structures of the eye. The illumination may also be in a dark-filed configuration such that the illumination sources are directed to the independent surfaces outside the capture numerical aperture of the image portion of the video system. Alternatively the illumination may also be in a bright field configuration. In both the dark and bright field configurations, the illumination light source can be used as a fixation beam for the patient. The illumination may also be used to illuminate the patient's pupil to enhance the pupil iris boundary to facilitate iris detection and eye tracking. A false color image generated by the near infrared wavelength or a bandwidth thereof may be acceptable.

The illumination light from the illumination light source 118 is transmitted through the beam combiner 120 to the beam combiner 90. From the beam combiner 90, the illumination light is directed towards the patient's eye 43 through the objective lens assembly 94 and through the patient interface 94. The illumination light reflected and scattered off of various structures of the eye 43 and patient interface travel back through the patient interface 94, back through the objective lens assembly 94, and back to the beam combiner 90. At the beam combiner 90, the returning light is directed back to the beam combiner 120 where the returning light is redirected toward the camera 116. The beam combiner can be a cube, plate or pellicle element. It may also be in the form of a spider mirror whereby the illumination transmits past the outer extent of the mirror while the image path reflects off the inner reflecting surface of the mirror. Alternatively, the beam combiner could be in the form of a scraper mirror where the illumination is transmitted through a hole while the image path reflects off of the mirrors reflecting surface that lies outside the hole. The camera 116 can be a suitable imaging device, for example but not limited to, any silicon based detector array of the appropriately sized format. A video lens forms an image onto the camera's detector array while optical elements provide polarization control and wavelength filtering respectively. An aperture or iris provides control of imaging NA and therefore depth of focus and depth of field and resolution. A small aperture provides the advantage of large depth of field that aids in the patient docking procedure. Alternatively, the illumination and camera paths can be switched. Furthermore, the aim light source 110 can be made to emit infrared light that would not be directly visible, but could be captured and displayed using the video subsystem 92.

Figure 12:
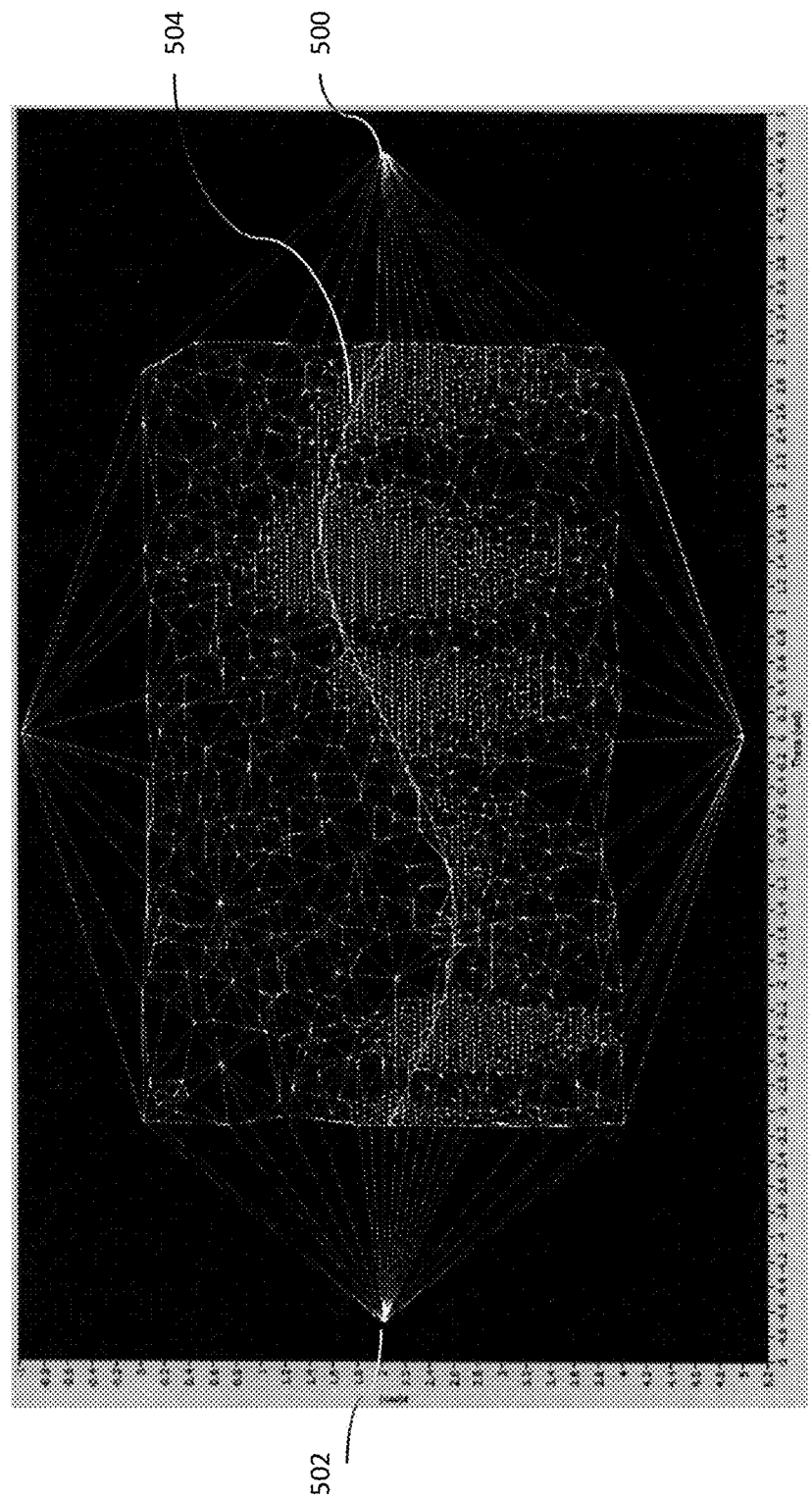
FIG. 12 is a plot of the image data set from a raster scan of a human eye showing the segmentation of the data set.
Figure 13:
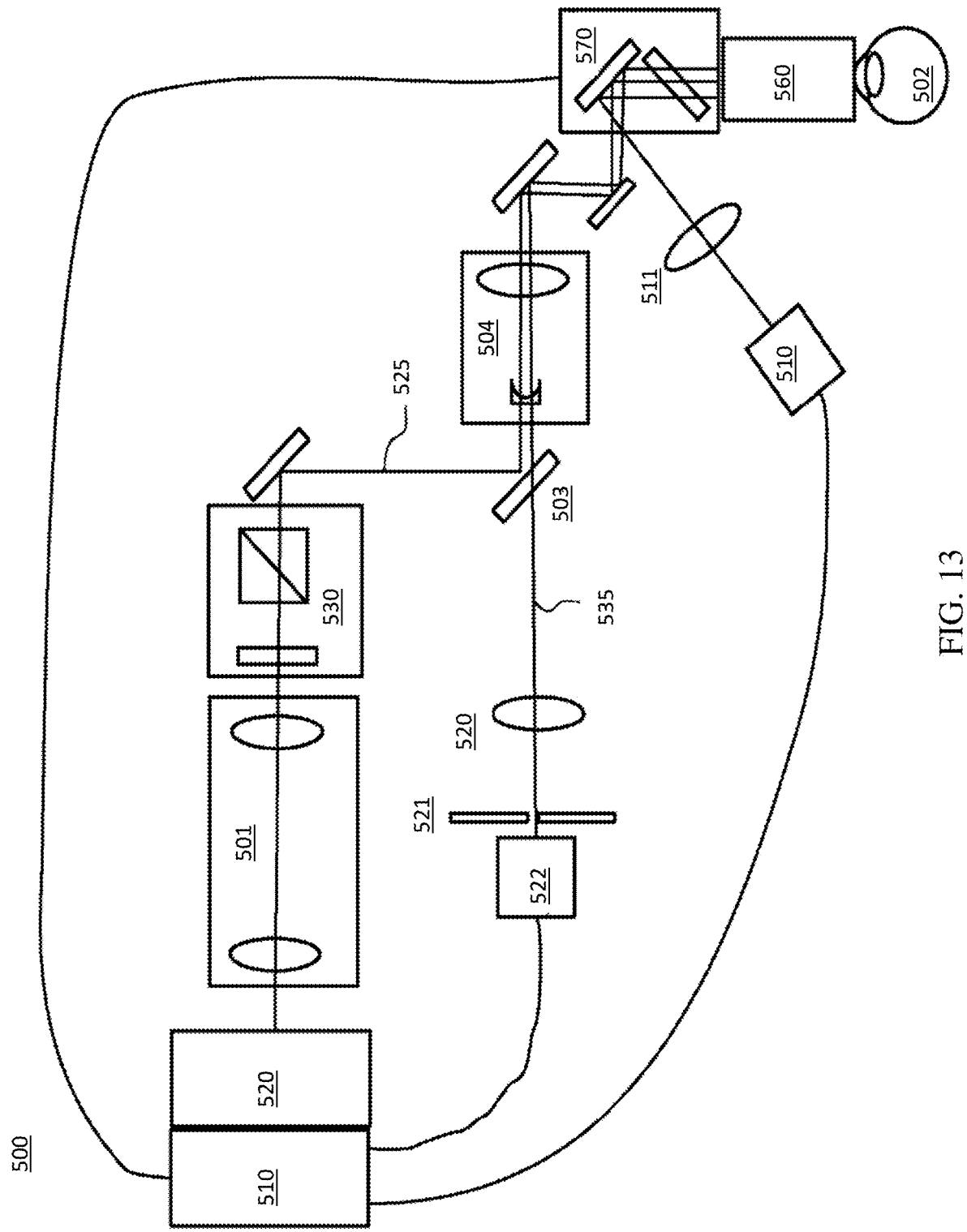
FIG. 13 is another illustration of a system in accordance with an embodiment of this invention.

The present invention alternatively can be implemented by a system 500 that does confocally detects back reflected or autofluoresence for imaging of the patient's eye 502, such as the system shown in FIG. 13. The system 500 includes control electronics 510, a light source 520, an attenuator 530, a beam expander 501, an optical variable beam attenuator 530, an separate focus lens combination 504 and a beam reflection and scanning means 570. The light beam 525 of light source 520 is focused through focusing lens 560 to its target location 502. This will be controlled by electronics 510 which is connected to deflection unit 570. Additionally the auto fluorescence light 535 of the target structure 502 is de-scanned by the similar optical path shared with laser light 525 by preferred means of a dichroic beam splitter 503 and focused by a lens 520. An aperture pinhole 521 is placed in the focal spot of formed beam 535 as a conjugate of the laser beam 525 in target structure 502. The intensity of the transmitted auto fluorescence light through beam aperture 521 is detected and converted to an electrical signal which can be read by the control unit 510. Also an image of the treated area is imaged by lens 511 on an image capture device 510 which can be a CCD or a CMOS camera. Also this signal is transmitted to control unit 510. In the embodiment of FIG. 12, similarly named components, such as light source 520, have the same or similar structure as those discussed above with respect to FIGS. 2-4 as would be understood by those ordinarily skilled.

In another variation of system 500, the detection combination unit 503, 520, 521, 522 is used to confocally detect the back reflected light 535 of beam 525 from sample 520 for imaging of the target structure 502, such as a target tissue with the eye of a patient. In this embodiment, the target tissue may be imaged by raster scanning at least a portion of the target structure 502 with the beam 525 to provide for a plurality of data points, each data point having a location and intensity associated with it. In some embodiments, the raster scan selected to deliver a sparse pattern in order to limit the patient's exposure, while still discerning a reasonable map of the intraocular targets. When a confocal imaging arrangement is used, the treatment laser beam (i.e. the laser beam having the parameters suitably chosen as described above for the modification of tissue) is preferably attenuated to the nanoJoule level and used for imaging of the structures to be imaged instead of the OCT system described above. When used for imaging, the attenuated laser beam may be referred to as an imaging beam. In many embodiments, the treatment beam and the imaging beam may be the same except for the pulse energy of the laser source is lower than the treatment beam when the laser beam is used for imaging. In many embodiments, the pulse energy of the laser beam when used for imaging is preferably from about 0.1 nJ to 10 nJ, preferably less than 2 nJ and more preferably less than 1.8 nJ. The use of the same laser beam for both treatment and imaging provides for the most direct correlation between the position of the focal locations for imaging and treatment— they are the same beam. This attenuated probe beam can is preferably used directly in a back reflectance measuring configuration, but, alternatively, may be used indirectly in a fluorescence detection scheme. Since increases in both backscatter and fluorescence within tissue structures will be evident, both approaches have merit.

In a preferred embodiment, imaging of a first target area to be modified is performed sequentially with the modification of the tissue in the first target area before moving on to a second, different, target area, i.e. imaging is performed sequentially with treatment in a predetermined target area. Thus, for instance imaging of the lens capsule is preferably followed by treatment of the lens capsule before imaging is carried out on other either structures, such as the cornea or iris. In another embodiment, imaging of a first target area where a first incision to be place is performed sequentially with the scanning the treatment beam to perform the incision in the first target area before moving on to a second target area for performing a second incision, i.e. imaging of the area to be incised is performed sequentially with scanning the treatment beam to perform in the predetermined target area.

In another embodiment, a cataract procedure comprises a capsulotomy incision, and at least one of a cataract incision and a limbal relaxing incision. In one embodiment, imaging of the target tissue where the capsulotomy is to be performed is followed by scanning of the treatment to perform the capsulotomy, and then the treatment beam is scanned to perform the capsulotomy. Subsequently, imaging of the target tissue where the at least one of the cataract incisions (CI) and the limbal relaxing incision (LRI) is carried out and then the treatment beam is scanned to perform the at least one of the LRI and the CI. When an LRI is selected, this minimizes the chance for the patient to move between imaging and treatment for the LRIs which are the most critical/sensitive to eye movements between image and treatment.

Figure 5:
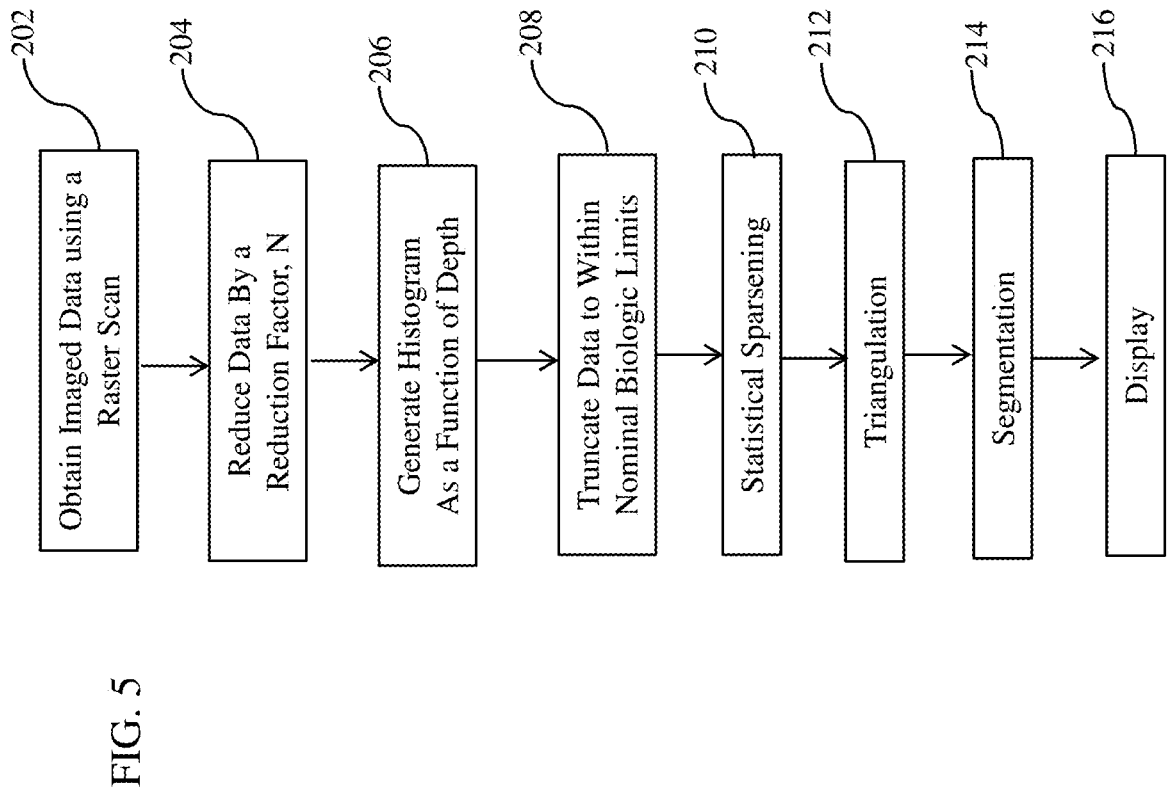
FIG. 5 is a simplified block diagram showing steps involved in many embodiments of the imaging processing method and system.

The methods described herein may include one or more acts or steps shown in FIG. 5 and described in more detail herein. Each block in FIG. 5 may alternatively be considered either a step in an imaging method, a step in an image processing method or an act carried out by a imaging processing system, by for instance, a processor carrying out a set of instructions. Thus, methods and/or steps/acts herein may include for instance one or more of the following: a Step 202 of obtaining image data by raster scanning a sample to be imaged; a Step 204 of reducing the image data by a reduction factor, N; a Step 206 of generating a histogram of the image data as a function of depth in the sample to be imaged; a Step 208 of truncating the image data according to within one or more nominal biologic limits; a Step 210 of statistical sparsening; a Step 212 of triangulating of the statistically sparsened image data; a Step 214 of segmenting the triangulated image data to identify an edge, boundary, or feature within the sample to be imaged; and a Step 216 of displaying the image data, including the segmentation of the image data to the user.

In another embodiment, an image processing system includes a memory for storing a plurality of instructions and a processor for executing the instructions to perform a plurality of steps, the plurality of step comprising one or more steps/acts shown in FIG. 5 and described in more detail herein. The image processing system may optionally be incorporated into a laser surgical system such as laser surgical system 2. For instance, the memory of the image processing system may be memory 57 of system 2 and the processor of the image processing system may be processor 55 of FIG. 3. Alternatively, the memory and processor may be separate from system 2. For instance, image data may be obtained on system 2, and a separate imaging processing system may include a processor with instructions to receive the image data obtained on system 2 and to store the image data in a memory.

In another embodiment, a computer-readable, non-transitory medium storing a computer program for image processing is disclosed herein. The computer-readable, non-transitory medium comprises a computer program which causes a computer to execute a process comprising one or more steps shown in FIG. 5 and as described herein. The computer-readable non-transitory medium may be included as part of system 2. Alternatively, the computer-readable medium may be separate from system 2. For instance, image data may be obtained on system 2, and the program may include instructions to receive the image data obtained on system 2 and to store the image data in a memory.

In some embodiments, a Step 202 comprises obtaining image data by conducting a raster scan of the object to be imaged. In many embodiments, the object to be imaged is a biological tissue, and, in many embodiments, a human biological tissue. In many embodiments, the object to be imaged is a human eye.

In many embodiment, the imaging systems of the present invention include the necessary light source, optics and control systems to conduct the raster scan and obtain the image data. Suitable light sources, optics and control systems include, but are not limited to, the cutting laser 44, the shared optics 50, control electronics 54, and control panel/GUI 56 described above with respect to FIGS. 2-4. Alternatively, the raster scan and resulting image data may be carried out on a separate systems and provided to the imaging systems described herein to be used in connection with the imaging methods described herein.

A raster scan may be defined as a 3-dimensional tracing of a laser light source along the object to be imaged. In many embodiments, the raster scan is a scan pattern in which the laser light source is swept continuously along an area to be imaged, scanned from side to side in lines from top to bottom in a planar section, and then repeated in depthwise steps in the tissue to be imaged. When used in connection with a pulsed laser source, a pattern of closely spaced confocal intensity measurements resulting from separate laser pulses may be used to form an image.

Figure 6:
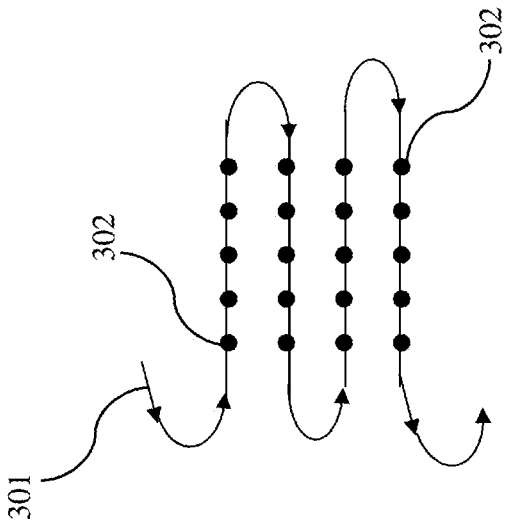
FIG. 6 shows a raster scan having a light source path comprised of laser pulses at spaced intervals.

FIG. 6 represents a raster scan having a light source path 301 comprised of 302 laser pulses spaced interval. In many embodiment, each spot 302 in FIG. 6 represents a confocal intensity measurement, each having its origin as a separate laser pulse. The distance between each spot 302 is a function of the sweep speed of the laser light source along path 301 and the pulse repetition rate of the laser surgical system. In ophthalmic applications, the pulse repetition frequency of the laser source can generally vary from 10 kHz to 250 kHz, or alternatively, between 50 to 200 kHz, or between 75 to 150 kHz. In some embodiment, a pulse picker may be used to limit the portion of laser pulses that are directed to the object to be imaged.

In a preferred embodiment, image data is collected on a point by point (i.e., pixel by pixel) basis by raster scanning the focus of a pulsed laser beam across a surface of the tissue to be imaged and detecting an intensity signal for each laser pulse corresponding to an intensity of, for instance, the light reflected from the location each laser pulse was respectively focused. The intensity of the light measured may alternatively be intensity of the light emitted by the tissue to be imaged either by fluorescence or phosphorescence of the target tissue after irradiation by the laser light beam. The resulting image data may comprise a set of data points, P, such as pixels, each data point $p_i$ in the data, $p_i \in P$, corresponding to a unique, discrete location (x,y,z) within the object to be issued and having an associated intensity, I, at the location. These data points may be referred to herein as image data. The set of data points therefore generally comprise at least one location datum and one intensity datum. The location of the laser pulses at coordinates (x,y,z) are connected in 3D space along the predetermined raster scan pattern, the design of which is delimited by the velocities and accelerations of the mirrors that are generating the trajectory of the laser scan.

In a preferred embodiment, the laser light source used to image the tissue is the same laser light source used for carrying out an incision. One specific embodiment is a system for ophthalmic surgery, comprising a laser source configured to deliver a laser beam comprising a plurality of laser pulses having a wavelength between about 320 nanometers and about 430 nanometers and a pulse duration between about 1 picosecond and about 100 nanoseconds. An optical system is operatively coupled to the laser source and configured to focus and direct the laser beam in a pattern into one or more tissue structure targets within an eye of a patient. In some embodiments, the interaction between the one or more targets and the laser pulses is characterized by linear absorption enhanced photodecomposition without formation of a plasma or associated cavitation event. An integrated imaging subsystem that captures in a confocal arrangement backreflected light from a sample is provided by the laser source. The laser pulses may induce fluorescence that is collected by the imaging subsystem. The system may be configured to provide interleaved lower energy pulses for imaging and higher energy pulses for treatment. The imaging subsystem may comprise an optical coherence tomography system, a Purkinje imaging system, and/or a Scheimpflug imaging system. The system may further comprise a controller configured to determine the locations and shapes of ocular structures, to determine pattern placement and/or laser parameters, and position the patterns within the defined targets.

The raster scan may be determined by consideration of the resolution of the image to be obtained. In many embodiments, the resolution of the image data is preferably at least 100 microns/pixel, or alternatively, at least 50 microns/pixel, or at least 25 microns/pixel, or at least 10 microns/pixel. In ophthalmic applications, a resolution of at least 50 microns/pixel may be satisfactory for many surgical applications. Thus, in one example, the resolution of the image data is set at 50 microns/pixel. When the resolution is set at 50 microns per pixel, the spot spacing in the raster scan is set at 50 microns and the line spacing is also set at 50 microns.

The raster scan need not be designed to obtain a rectangular data set but may produce a data set of any shape sufficient to image the portion of object to be imaged. This makes it possible to simplify raster scanning of the tissue to be imaged. Without an added requirement that the data obtained from points on a scan align with the previous line or subsequent lines, one can, for instance, maintain the scan at the same velocity wherever one desires to trace a raster line and obtain intensity data at, for instance, regular intervals along even a conical surface because there is no need to produce a rectangular data set. Further, when the laser is turning around one can use the fastest achievable velocity between lines. This can be achieved because there is no additional requirements of having points on a raster line align with corresponding points on a prior raster line in rectangular space.

In many embodiments, the number of data points contained in the data set to be processed is reduced by one or more steps. The data point reduction steps may include one more steps of (1) data point averaging of the pixel data (FIG. 5, Step 204); (2) truncating the data set to remove data points scanned at positions outside nominal biologic limits (FIG. 5, Steps 206 and 208); and (3) selectively removing a data points from amongst the set of image data points based on an assigned probability that that the data will be retained in the data set (FIG. 5, Step 210, "Statistical Sparsening"). In the statistical sparsening step, an assigned probability is dependent upon its intensity.

The purpose of the removing individual image data points is to reduce the size of the data set and thus to minimize the size of the calculations and the time required to perform them. In many embodiments, the preferred methods for reducing the amount of image data to process involves selectively removing individual data points based on their intensity. This is because image data with little intensity is unlikely to be contribute much image information relating to the structure to be imaged in the image processing, but image data having larger intensities is likely to have more image information, thus a method which selectively retains image data points based on intensity is more likely to retain individual data points having image information in the data set. In connection with many embodiments, it is possible to remove image data based from a data set without having to maintain the image data in a rectangular format.

Optionally, the imaging methods and systems of the present invention may optionally include a Step 204 of reducing the data by a reduction factor, N. In connection with this step, a reduction factor N is applied to the data set, P, and generally comprises averaging the position and intensity data for N consecutive position locations in the data set. For example, where a reduction factor of N is applied to a data set comprised of an array of pixels, each having a location (x,y,z) and an intensity (I, on a scale from 0-255), the locations and intensities of N successive locations in the data array are averaged. Thus, for example, the average value of the X position, $\bar{x}$, of the first N pixels in the pixel array is calculated, the average value of the Y position, $\bar{y}$, of the first N pixels in the pixel array is calculated, the average value of the Z position, $\bar{z}$, of the first N pixels in the data array is averaged, and the average value intensity, $\bar{I}$, of the first N pixels in the pixel array is calculated. This procedure then continues for the entirety of the data set (i.e., pixel array) to yield a reduced data set comprised of the average positions ($\bar{x}, \bar{y}, \bar{z},$) and a corresponding average intensity, $\bar{I}$, that subsequently replaces the original data set in any subsequent imaging steps. This replacement data set obtained by application of the reduction factor is preferably used for all subsequent image processing steps.

The reduction factor will not usually be applied where all of the collected data points are necessary in order to achieve an image having the required resolution. Rather, the reduction factor is preferably applied where the number of data points collected are greater than the number of data points required to obtain an image of the desired resolution. In these instances, the maximum reduction factor may be calculated by comparing a predetermined resolution, R, to the spacing, S, between nearest neighbors in the data point set. Thus, for instance, in the case of a pulsed laser imaging system, the reduction factor N can be determined by comparing the desired resolution of the image, R, with the spacing between two nearest laser pulses in the data set, S, according to the following formula:

$$N = \frac{R}{S}$$

Thus, for instance, in a pulsed laser imaging system, if the desired resolution, R, of the image if 50 microns, and the spot spacing, S, of the discrete laser pulses is 5 microns (and assuming that confocal intensity is measured at each spot), the reduction factor, N is 10. Of course, as one of ordinary skill would appreciate, one could choose a reduction factor smaller than N, and so, the reduction number calculated according to this formula may actually be considered a maximum reduction number.

In many embodiments, the imaging processing methods and systems may include a step of eliminating data points collected from raster scanning positions outside physically relevant limits in the sample. In the case of ophthalmic applications, this may include a step of generating a histogram as a function of depth (FIG. 5, Step 206) and truncating the data so that the data set is confined to data points in the data set that are within nominal biological limits (FIG. 5, Step 208). In many embodiments, the depth is measured in a direction from the anterior of the eye to posterior of the eye along the optical axis of the eye. These steps are preferably, but not necessarily, carried out after any reduction in the data set by a reduction factor, N (FIG. 5, Step 204).

Figure 7B:
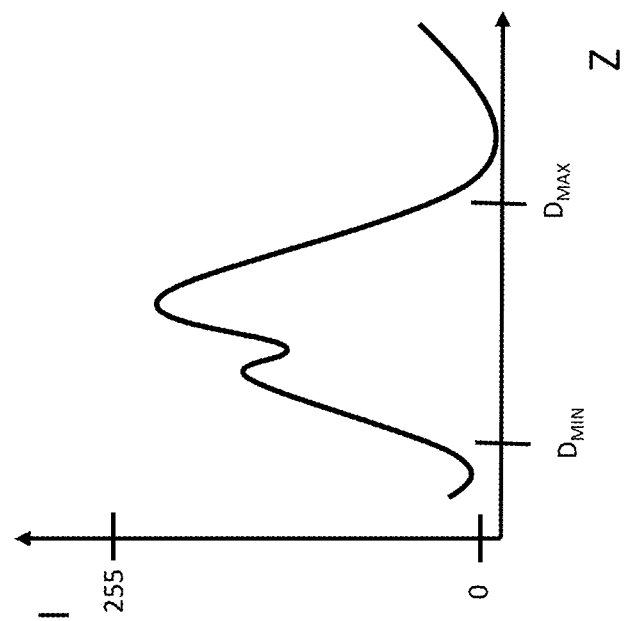
FIG. 7B is a graphical representation of a histogram of an image data set as a function of depth.
Figure 7A:
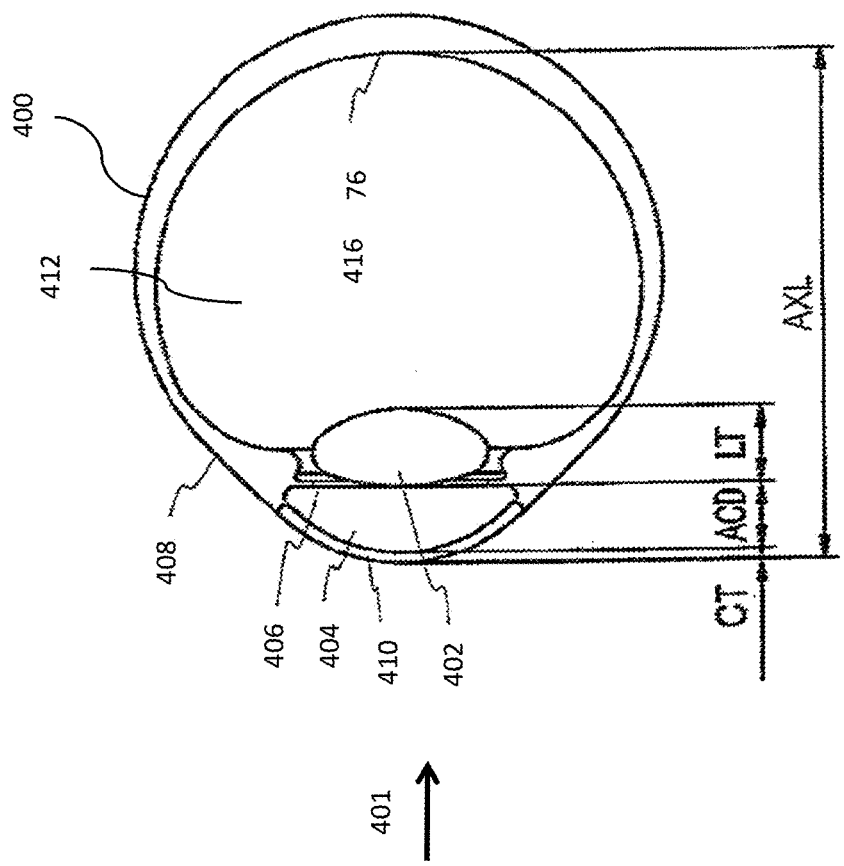
FIG. 7A is a schematic drawing of a human eye.

The reduction of the data points in the data set in Steps 206 and 208 may be illustrated with respect to FIGS. 7A and 7B.

FIG. 7A is a schematic drawing of a human eye 400. In many embodiments, a light beam 401 from a laser light source enters the eye from the left of FIG. 10A, refracts into the cornea 410, passes through the anterior chamber 404, the iris 406 through the pupil, and reaches lens 402. After refracting into the lens, light passes through the vitreous chamber 412, and strikes the retina 476, which detects the light and converts it to an electric signal transmitted through the optic nerve to the brain (not shown). The vitreous chamber 412 contains the vitreous humor, a clear liquid disposed between the lens 402 and retina 416. As indicated in FIG. 10A, cornea 410 has corneal thickness (CT), here considered as the distance between the anterior and posterior surfaces of the cornea. Anterior chamber 404 has anterior chamber depth (ACD), which is the distance between the anterior surface of the cornea and the anterior surface of the lens. Lens 402 has lens thickness (LT) which is the distance between the anterior and posterior surfaces of the lens. The eye has an axial length (AXL) which is the distance between the anterior surface of the cornea and the retina 416.

The anterior chamber 404 is filled with aqueous humor, and optically communicates through the lens with the vitreous chamber, which occupies the posterior ⅘ or so of the eyeball and is filled with vitreous humor. The average adult eye has an ACD of about 3.15 mm, with a large variability between individuals. The average adult eye has an AXL of about 24 mm. The average thickness of the lens, which varies with age, is about 4 mm, while the average equatorial diameter of the lens is about 9-10 mm.

In most ophthalmic imaging applications, the imaging is not carried out over the entire depth of the eye along the optical axis simultaneously. Rather, the imaging is carried out on a discrete portion of the eye, such as the lens or the cornea, which will be the subject of the eye surgical procedure. Different portions of the eye may be imaged sequentially. However, a user may define the field of scan over a biological area larger than is necessary to produce a suitable image of the object to be imaged. Thus, in the case that a lens 402 is to be imaged, a user may define the scan from a region well within the anterior chamber 404 to a region well within the vitreous chamber 412. However, the inclusion of the data points in these regions is not only of marginal use but also increases the size of the calculation and the time required to perform it.

As a result, many embodiments include a step of generating a histogram as a function of depth (FIG. 5, Step 206) and truncating the data to within the biological limits (FIG. 5, Step 208). This is illustrated conceptually in FIG. 7B. In FIG. 7B, the intensity of image data is plotted as a function of axial depth (Step 206). Then, the data points having a z value of less than $D_1$ or greater than $D_2$ are removed from data set.

As a general rule, the points at which the data should be truncated, i.e., at $D_{min}$ and $D_{max}$ in FIG. 7B, are based on empirical eye measurements of the patient population. In general, the relevant distance in a number of eye in the patient population are measured and these are subsequently used to generate average eye nominal distances and population variations in the nominal distances. For instance, eye measurements, such as lens thickness, can be performed and collected on the large numbers of the patient population, the average lens thickness and variations of the lens thickness within the patient population can be measured. Once the average measurement and its variations are generated in the field, empirical ranges that capture more than 90%, or alternatively more than 95%, or 99% or 99.99% percent of the patient populations can be developed. These empirical ranges in patient population are referred to herein as nominal biological limits and can then be applied to the collected data set to truncate the data set to retain those data points only within the limits of the empirical ranges and to remove those data points outside of the nominal limits. The data set obtained by the reduction of the data to only those data points comprises a replacement data set that is preferably used in all subsequent imaging steps.

By way of example, in one embodiment a first reduced data set from Step 204 is used to generate a histogram. A histogram is the distribution of the intensity of the data set as a function of the depth. Data points from the reduced data set having either a depth less than $D_{min}$ or a depth greater than $D_{max}$ are removed from the data set, thereby producing a second reduced data set. This second reduced data set replaces the first reduced set in all subsequent image processing steps.

In many embodiment, the image processing methods and systems include a step of statistical sparsening (FIG. 5, Step 210). The Step 210 of statistical sparsening may be done after the optional steps of reducing the data set by a reduction factor, N (Step 204) and the steps of truncating data that falls outside of nominal biologic distances (Step 208). Where one or all of these steps are performed, the data that is subject to statistical sparsening process is the set of data points remaining in the data set after completion of the those prior steps. Alternatively, statistical sampling may be performed on all the data that is obtained from the raster scan.

In statistical sparsening, each point in the data set is assigned a probability of being retained in the data set for further image processing, or alternatively a probability of being removed from the data set for further image processing (e.g., triangulated in Step 212), based on its measured intensity. Without being limited to theory, in the statistical sparsening step, a likelihood that a data point contains image information is correlated with its intensity measurement. Thus, data points having a relatively higher measured intensity signal have a higher probability of containing image information and therefore should have a higher probability of being retained in the data set to be processed (i.e., triangulated in Step 212). Conversely, data points having a lower measured intensity signal have a lower probability of containing image information and therefore should have a lower probability of being retained in the data set to be processed (i.e., triangulated). As a result, data points having a high probability of containing image information are likely to be retained in the data set for image processing and data points that are unlikely to contain image information are likely to be removed in the data set for image processing.

Figure 8:
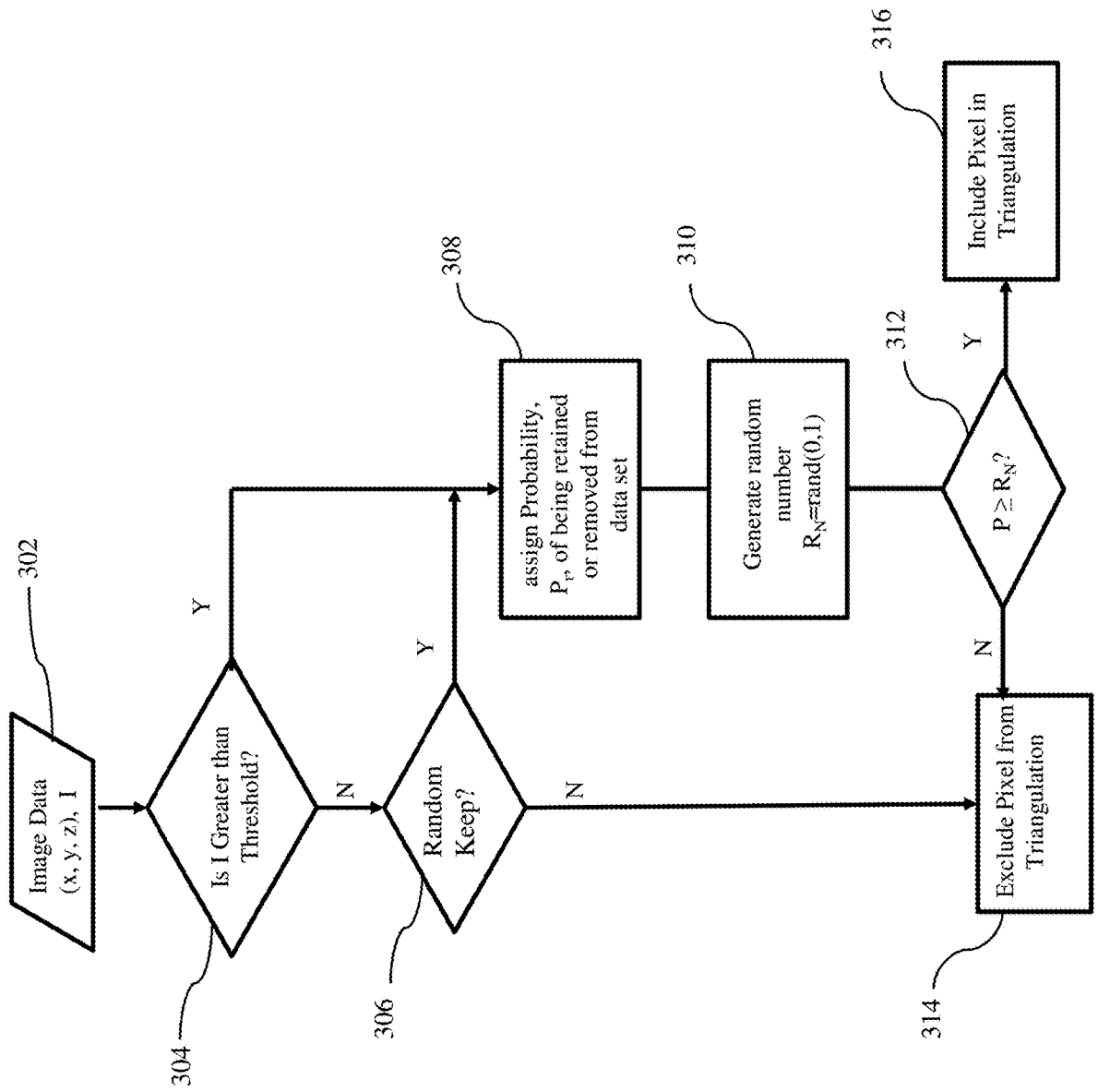
FIG. 8 is a block diagram showing certain steps of the statistical sparsening of the data set of many embodiments.

The statistical sparsening procedure is outlined in FIG. 8. A first optional step 304 compares the measure intensity of a data point, I, of a data point against a predetermined threshold intensity value, $I_{Th}$. If the value of the measured intensity is above the predetermined threshold, i.e., $I > I_{th}$, the data point is assigned probability of being retained or removed from the data set according to Step 304. If the value of the measured intensity is lower than the predetermined threshold, $I < I_{th}$, the data point is generally exclude from further imaging processing at Step 314. Intensities equal to the threshold may be included or excluded from Step 304 without significant differences in effectiveness of the procedure. However, an optional Step 306 may be included that randomly includes a percentage of the data points having measured intensities below the predetermined threshold in Step 304.

In some embodiments, the threshold value is 50 or less on an intensity scale of 1 to 255, or alternatively, 10 or less, or alternatively, 1 or less, or 0.5 or less. In an embodiment of the example disclosed herein, the threshold value is 0.015.

At step 304, a probability function, P(I), transforms the intensity associated with a data point into a probability, P, of being retained in the data set (or, alternatively, a probability of being removed from the data set). The probability obtained from the probability function for each data point is on a scale of $Pr_{max}$ to $Pr_{min}$, where $Pr_{min}$ means there is no probability the data point will be retained in the data set for further image processing and $Pr_{max}$ corresponds to a 100% probability that the data point will be retained in the data set for further image processing. Preferably, $Pr_{min}=0$ and $Pr_{max}=1$.

Figure 9:
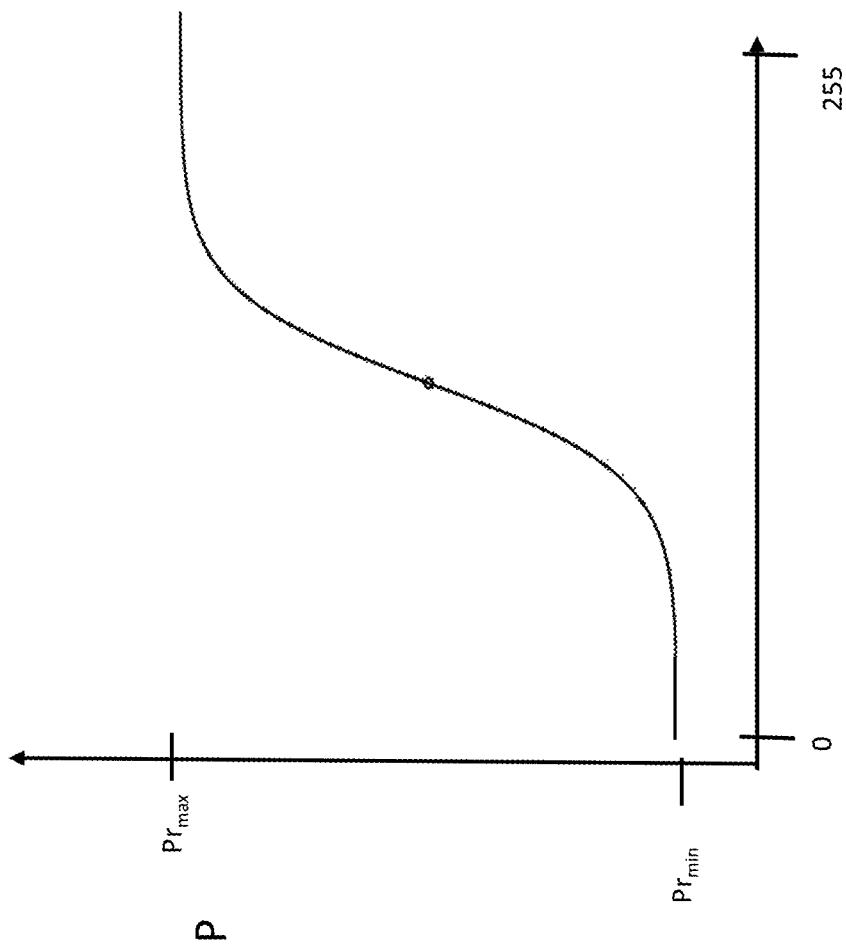
FIG. 9 is a graphical representation of a sigmoid function used to assign a probability of being retained in the data set according to many embodiments of the image processing method and system.

As shown in FIG. 9, the probability function that transforms the intensity into a probability preferably has the shape of a sigmoid function. The sigmoid function is an S-shaped form defined by the equation, $$S(t) = \frac{1}{1+e^{-t}}$$

and a number of polynomials have been generated that approximate the sigmoid shape. In a preferred embodiment, the polynomial used to generate the probability of the data point being retained in the data set is as follows:

$$y(t) = at^3 + bt^2.$$

The parameters a and b may be empirically determined based on an individual application. In a preferred embodiment, a=2 and b=3.

Then, at Step 310 of FIG. 8, a random number generator generates random number, $R_N$, from within the range of $Pr_{min}$ to $Pr_{max}$ and the value of $R_N$ and is compared with the probability P that a data point, the point goes or stays according to the probabilities. Thus, if $Pr \geq R_N$, the data is retained in the data set for further image processing and if $Pr < R_N$, the data point is not included in the data set to be used for further image processing.

The statistical sparsening has the effect of removing a large percentage of data points that do not contain image information, while retaining a large percentage of those that do. This cannot be done in image processing techniques requiring a rectangular image structure because the removal of data points from within the data set very likely will destroy the rectangular shape of the data set. As a result of statistical sparsening, the set of points where the information of the image is increased and the set of points likely to be of limited value in image processing are removed.

The reduced data set obtained as a result of the statistical sparsening comprises a replacement data set that is subsequently used in all image processing steps.

The reduced data set resulting Steps 204, 206, 208 and/or 210 are then triangulated. In addition, any end points necessary for segmentation of the data set in Step 214 should be added to the data set prior to triangulation. A triangulation according to the many embodiments should generally be a planar subdivision, preferably a maximal planar subdivision, whose faces are triangles and whose vertices are the data points of the data set obtained from statistical sparsening. The Delaunay triangulation is a known triangulation technique useable in connection with the present invention. See, e.g., Computational Geometry in C, Second Edition 1998, Joseph O'Rourke, Cambridge University Press, Chapter 5. Although many embodiments use Delaunay triangulation, other triangulation algorithms may also be suitable for subsequent segmenting or cutting the triangulated image.

In the Delaunay triangulation, a data set, P, comprises a set of points in the plane, and T is a Delaunay triangulation of P if and only if the circumcircle of any triangle of T does not contain a point of P in its interior. More specifically, in the Delaunay triangulation, three points $p_i, p_j, p_k \in P$ are vertices of the same face of the Delaunay graph of P if and only if the circle through $p_i, p_j, p_k$ contains no point of P in its interior. Further, two points $p_i, p_j \in P$ form an edge of the Delaunay graph of P if and only if there is a closed disc C that contains pi and pj on its boundary and does not contain any other point of P. There are a variety of known algorithms that may be used to implement the Delaunay triangulation known to those ordinarily skilled.

The Delaunay triangulation of the remaining data set provides a Delaney Graph comprising a set triangles comprising nodes and edges connecting the nodes, in which the data points of the remaining data set comprise the set of nodes in the Delaunay Graph and edges that connect each node with adjacent nodes to define the vertices of triangles.

After the data set are triangulated at Step 212, the triangulated graph of the data points is segmented at FIG. 5, Step 214. For example, in many embodiments, edges in the Delaunay graph derived from Step 212 are associated with respective weights, or costs, and segmentation includes cutting the graph by determining a minimum weight path that connects two endpoints. Computationally efficient techniques including, for example, Dijkstra's algorithm can be used to determine the lowest weighted path of a graph between arbitrary endpoints. In brief, Dijkstra's algorithm is a graph search algorithm that solves the single-source shortest path problem for a graph with non-negative edge path costs, producing a shortest path tree. For a given node in the graph, the algorithm finds the path with lowest cost (i.e., the shortest path) between that vertex and every other vertex. It can also be used for finding costs of shortest paths from a single vertex to a single destination vertex by stopping the algorithm once the shortest path to the destination vertex has been determined. See Dijkstra, E. W. (1959). "A note on two problems in connexion with graphs," Numerische Mathematik 1: 269-271; Cormen, Thomas H.; Leiserson, Charles E.; Rivest, Ronald L.; Stein, Clifford (2001), "Section 24.3: Dijkstra's algorithm," Introduction to Algorithms (Second ed., MIT Press and McGraw-Hill. pp. 595-601). Although many embodiments use Dijkstra's algorithm, other shortest path algorithms may also be suitable for segmenting or cutting the triangulated image.

An important aspect of accurately segmenting a graph is to assign the appropriate edge weights. Metrics for varying weight values include functions of distances between pixels or differences between intensity values. In many embodiments, it is preferred to define the cost as the function of the inverse of the average intensity of the two nodes instead of using physical distance from, for example, node to node or node to the edge. In many embodiments, the cost for travelling the path from Node $X_1$ having Intensity $I_1$ and Node $X_2$ having the Intensity $I_2$ in the Delaunay Graph is as follows:

$$Cost = \frac{1}{(I_1 + I_2)/2}$$

As a result, a higher average intensity of the two nodes forming an edge in the Delauney graph results in a lower cost of the path in the Dijkstra algorithm. Conversely, a lower average intensity of two nodes forming an edge in the Delaunay graph of the data results in a higher cost of the path in the Dijkstra algorithm.

Segmenting a layer requires the selection or estimation of the corresponding layer's start and end nodes. Preferably, the endpoints are automatically initialized. Alternatively, endpoints may be manually selected by a user.

In many embodiments, endpoint initialization may be based on the assumption that the layer to be segmented extends across the entire width of the image. Since Dijkstra's algorithm prefers minimum-weighted paths, an additional set of nodes may be added to both sides of the image with arbitrary intensity values and minimal costs $C_{min}$ assigned to edges connecting the endpoint nodes to the image data points. Here, $C_{min}$ should be significantly smaller than any of the non-zero weights in the adjacency matrix of the original graph. In doing so, the newly added nodes maintain their connectivity, and the graph cut is able to traverse in the direction of these nodes with minimal resistance. This allows for the start and end nodes to be assigned arbitrarily, since the graph cut will move freely along these columns prior to moving across the image in the minimum-weighted path. It should be noted that the endpoints should be added to the data set to be triangulated in Step 212.

Once the graph is segmented, the segmented image may be displayed to a user in FIG. 5, Step 216.

Example

Imaging a Capsulotomy in a Human Lens

Cataract extraction is one of the most commonly performed surgical procedures in the world with estimates of 3.5 million cases being performed annually in the United States and 15 million cases worldwide. Modern cataract surgery is typically performed by first creating an opening in the cornea and then another in the anterior lens capsule, which is termed an anterior capsulotomy or capsulorhexis. The lens capsule is a membrane that surrounds the lens and is generally about 50 microns thick. The patient's natural crystalline lens is then typically removed by ultrasonic phacoemulsification and irrigation/aspiration methods and a synthetic foldable intraocular lens (IOL) ultimately inserted into the now empty capsular bag.

The concept of the capsulotomy is to provide a smooth continuous circular opening in the lens capsule through which not only the phacoemulsification of the nucleus can be performed safely and easily, but also for easy insertion of the intraocular lens. It provides both clear central access for insertion, a permanent aperture for transmission of the image to the retina by the patient, and also a support of the IOL inside the remaining capsule. The capsulotomy is the most technically demanding surgical step in the cataract removal procedure. The removal of the crystalline lens is the longest and most involved surgical step in the cataract removal procedure. It typically requires the use of appreciable amounts of ultrasonic energy to fragment the lens into pieces small enough to be easily aspirated away.

Figure 10B:
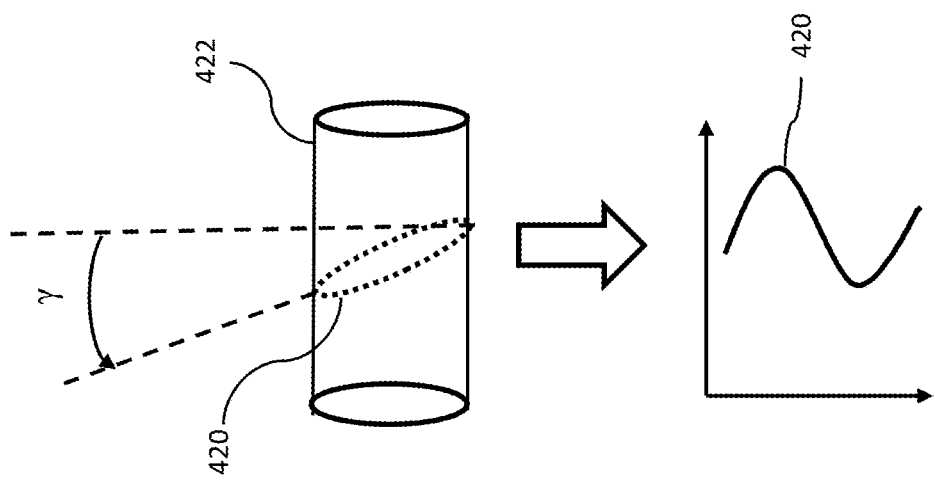
FIGS. 10A and 10B are graphical illustrations of certain aspects of imaging a capsulotomy in a tilted lens.
Figure 10A:
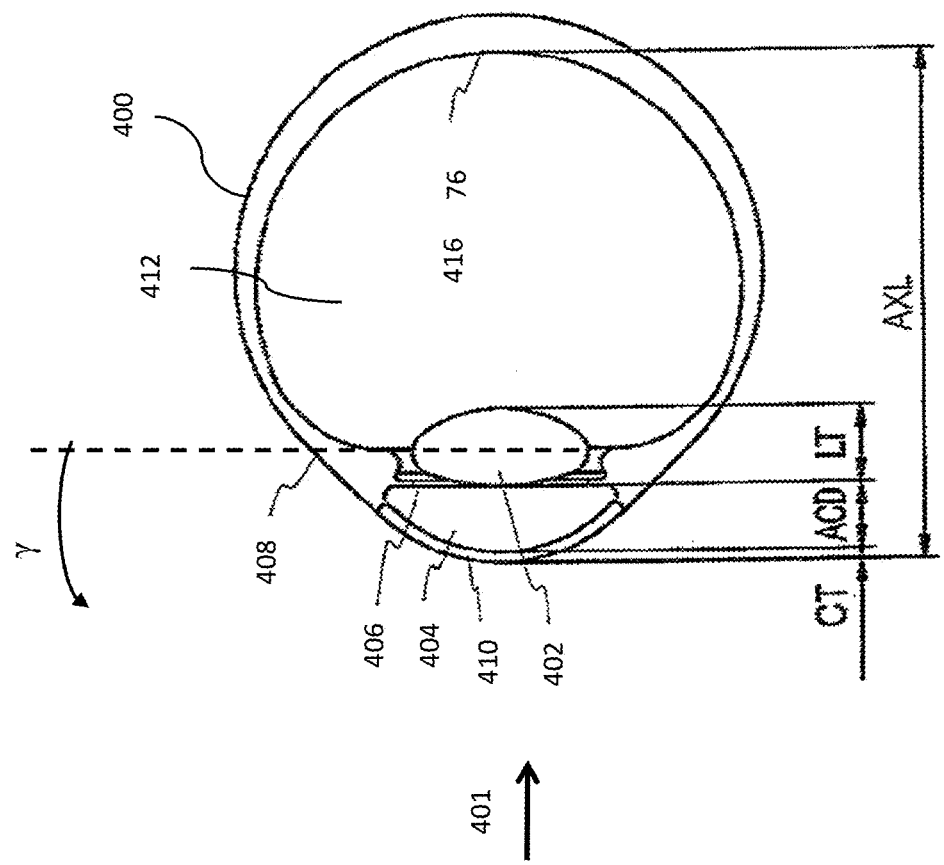

FIGS. 10A and 10B are intended to illustrate tilt of the human lens in order to demonstrate the anticipated features of an image of a capsulotomy when displayed graphically in two dimensions. FIG. 10A is an illustration of a human eye showing a lens 402 into which a circular capsulotomy can be incised in the anterior surface of the lens 402. FIG. 10B illustrates that, in many subjects the lens, including the lens capsule, may be tilted at an angle γ relative to the optical axis of the eye. The boundary of the capsulotomy incision 420 in the lens capsule can therefore be represented as the intersection of a plane with a cylinder 422 at an angle γ as shown in FIG. 10B. When the cylinder 422 is "unwrapped" for graphical presentation in 2D space as shown in the lower portion of FIG. 10B, the graph of the capsulotomy incision 420 is expected to have a sinusoidal shape.

Figure 11:
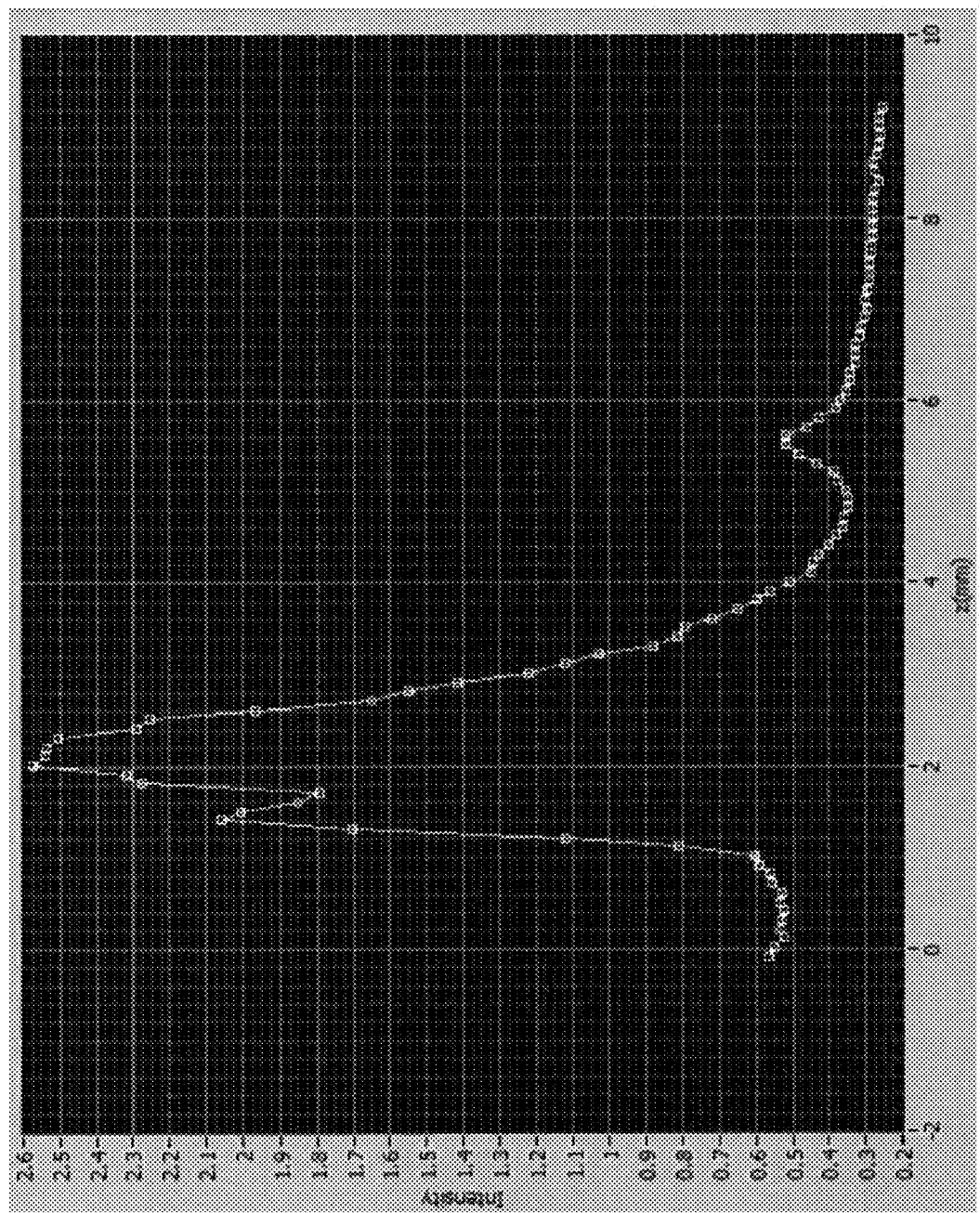
FIG. 11 is a histogram of an image data set from a raster scan of a human eye in which intensity is plotted as a function of depth.

FIGS. 11 and 12 are plots of image data from a capsulotomy scan taken of the eye of human subject that has undergone a capsulotomy. The capsulotomy imaging scan was done over a depth (along the axial length of the eye) of nine millimeters. This depth range extends from close to the cornea to position posterior to the lens. The desired resolution of the scan was 50 microns. The raster scan was conducted at line spacing of 50 microns and a spot spacing of 5 microns. The data was subjected to a reduction factor, N, of 10 (i.e. 50/5), and the reduced data set replaced the initial data set for the subsequent image processing step.

FIG. 11 shows a histogram of the image intensity data as a function of depth. In general, the lens capsule has an average thickness of fifty microns, and as shown in FIG. 10B, the tilt of the lens will create a sinusoidal distribution of the data. The nominal total amplitude of sinusoidal data that represents the tilt of the lens ranges from 1.4 mm to 2.6 mm. The data was truncated by removing data points falling outside a range of distance equal to the depth at maximum intensity, Imax, in the data set, ±2 mm to account for nominal biologic limits in the patient population. As shown in FIG. 12 $I_{max}$ occurs at a depth of about 2 mm. This truncated data set was used for all subsequent image processing.

Next, a statistical sparsening was used to evaluate of the intensity of each data point in the remaining data set. The intensity of each data point was compared to a predetermined threshold value, $I_{th}$. If the intensity of a data point was larger than a predetermined threshold value, $I_{th}$, the statistical sparsening process is continued. The threshold value in the example of the FIG. 11 was 0.015. If the intensity of a data point was below the intensity threshold value, $I_{th}$, the data point was removed from the data set.

If the intensity value of the selected point is greater than the threshold value, i.e., the statistical sparsening process was continued by assigning a probability, Pr, of keeping the data point (or alternatively, of rejecting the data point) based on its intensity, in the form of a polynomial which approximates the shape of a sigmoid. The polynomial used in the example of FIG. 11 is as follows:

$$y(t)=at^3+bt^2.$$

The parameters a and b may be empirically determined based on an individual application. In a preferred embodiment, a=2 and b=3.

The probability of keeping the data point was assigned a value between zero and one in accordance with the polynomial. Next, a random number, $R_N$, between zero to one was generated and if the assigned probability was greater than or equal to $R_N$, the data point was retained. If assigned probability was less than $R_N$, the data point was removed from the data set. This statistical sparsening analysis was applied to each point remaining in the data set. The data points remaining in the data set after the statistical sparsening process comprised a replacement data set that is then used in subsequent image processing steps.

The result of this process can be visualized by reference to FIG. 12, which is a plot of data points from the statistical sparsening. The statistical sparsening process results in a low density of data points (i.e., sparse areas) where the intensity of the data points is low and high density of data points in regions where the intensity point is high. For instance as one proceeds from top to bottom in FIG. 12 there is a region of relatively sparse data points at the top of the figure towards a region of higher density of data points in the middle and a region of sparse data points once again at the bottom of the figure a low intensity.

Next, beginning and end points, 500, 502 to be used in the Dijkstra analysis were added to the graph. The resulting data points, including end points 500, 502 are then used to generate a Delaunay Graph of the remaining data pints, thereby yielding a graph comprising a set of edges that connects the nodes.

The cost for travelling the path from Node $X_1$ having Intensity $I_1$ to Node $X_2$ having the Intensity $I_2$ in the Delaunay Graph was calculated as follows:

$$\text{Cost} = \frac{1}{(I_1 + I_2)/2},$$

and the Dijkstra algorithm was then applied to find the minimal path, which corresponded to the position in the image where the capsulotomy is located. FIG. 12 shows the resulting sinusoidal curve 504 of the minimal path that also is in the expected form a capsulotomy on a tilted lens.

This shows that the imaging process and system described herein is suitable for ophthalmic imaging.

It is to be understood that the present invention is not limited to the embodiment(s) described above and illustrated herein, but encompasses any and all variations explicitly and implicitly derived therefrom. Although not shown in the figures, multiple imaging steps can also be employed in between treatment steps to account for any changes in position and/or size due to treatment and further insure the accurate disposition of laser energy in the target tissue.

All patents and patent applications cited herein are hereby incorporated by reference in their entirety.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

The invention claimed is:

1. A system for imaging an object comprising:
   memory for storing a plurality of instructions; and
   a processor for executing the instructions to perform a plurality of steps, the instructions comprising:
   obtaining an image data set from a raster scan of the object, the image data set comprising a plurality of data points, each data point having a location and intensity associated with it;
   generating a reduced data set by selectively removing one or more data points from the image data set based upon an assigned probability of retaining the one or more data points in the data set, the assigned probability being a function of the intensity of a data point;
   generating a triangulation graph of the reduced data set as a planar subdivision having faces that are triangles that have vertices and edges, the vertices of which are the data points of the reduced data set and the edges of which are adjacent vertices; and
   segmenting the triangulation graph by finding a path with lowest cost between vertices of the triangulation graph, wherein the cost between vertices is a function of the respective intensity of the vertices.

2. The system of claim 1, wherein the object is a human eye.

3. The system of claim 1, wherein the instructions include instructions for reducing the image data set by a reduction factor prior to the selective removing the one or more data points.

4. The system of claim 1, wherein the instruction include instructions for truncating at least one of the image data set and the reduced data set by removing data outside nominal biologic limits from the selected data set.

5. The system of claim 1, wherein the planar subdivision is a maximal planar subdivision.

6. The system of claim 1, wherein the triangulation graph is a Delaunay graph.

7. The system of claim 1, wherein a cost associated with a first vertex having an intensity $I_1$ and a second vertex having an intensity $I_2$ is given by the formula $$\text{Cost} = \frac{1}{(I_1 + I_2)/2}.$$

8. The system of claim 1, wherein the instructions comprise instructions for finding the lowest cost path using a Dijkstra algorithm.

9. The system of claim 1, wherein the instructions include instructions for displaying the segmented data on a graphical user interface.

10. A laser eye surgical system comprising the system of claim 1.

11. A laser surgical system for imaging an object, comprising:
    a laser source for generating a pulsed laser beam;
    an imaging system comprising a detector;
    shared optics configured for directing the pulsed laser beam to an object to be sampled and confocally deflecting back-reflected light from the object to the detector;
    a controller operatively coupled to the laser source, the imaging system and the shared optics, the controller configured to:
    (a) scan the pulsed laser beam in a raster scan along the object to be imaged;
    (b) collect an image data set corresponding to the intensity of the back-reflected light from each of the laser pulses, the image data set comprising a plurality of data points, each data point having a location and intensity associated with it;
    (c) generate a reduced data set by selectively removing one or more data points from the image data set based upon an assigned probability of retaining the one or more data points in the data set, the assigned probability being a function of the intensity of a data point;
    (d) generate a triangulation graph of the reduced data set as a planar subdivision having faces that are triangles that have vertices and edges, the vertices of which are the data points of the reduced data set and the edges of are adjacent vertices; and
    (e) segmenting the triangulation graph by finding a path with lowest cost between vertices of the triangulation graph, wherein the cost between vertices is a function of the respective intensity of the vertices.

12. The system of claim 11, wherein the object is a human eye.

13. The system of claim 11, wherein the controller is configured to reduce the image data by a reduction factor prior to the selective removal.

14. The system of claim 11, wherein the controller is configured to truncate at least one of the image data set and the reduced data set by removing data outside nominal biologic limits from the selected data set.

15. The system of claim 11, wherein the planar subdivision is a maximal planar subdivision.

16. The system of claim 11, wherein the triangulation graph is a Delaunay graph.

17. The system of claim 11, wherein a cost associated with a first vertex having an intensity $I_1$ and a second vertex having an intensity $I_2$ is given by the formula $$\text{Cost} = \frac{1}{(I_1 + I_2)/2}.$$

18. The system of claim 11, wherein the controller is configured to find the lowest cost using a Dijkstra algorithm.

19. The system of claim 11, wherein the controller is configured to display the segmented data on a graphical user interface.

20. A computer-readable, non-transitory medium comprising a computer program which causes a computer to execute a process comprising:
   obtaining an image data set from a raster scan of the object, the image data set comprising a plurality of data points, each data point having a location and intensity associated with it;
   generating a reduced data set by selectively removing one or more data points from the image data set based upon an assigned probability of retaining the one or more data points in the data set, the assigned probability being a function of the intensity of a data point;
   generating a triangulation graph of the reduced data set as a planar subdivision having faces that are triangles that have vertices and edges, the vertices of which are the data points of the reduced data set and the edges of which are adjacent vertices; and
   segmenting the triangulation graph by finding a path with lowest cost between vertices of the triangulation graph, wherein the cost between vertices is a function of the respective intensity of the vertices.

* * * * *